(12) United States Patent
Drewes et al.

(10) Patent No.: US 8,163,511 B2
(45) Date of Patent: Apr. 24, 2012

(54) METHODS FOR THE IDENTIFICATION OF LRRK2 INTERACTING MOLECULES

(75) Inventors: Gerard Drewes, Heidelberg (DE); Carsten Hopf, Mannheim (DE); Valerie Reader, Cambridge (GB)

(73) Assignee: CellZome AG, Heidelberg (DE)

( * ) Notice: Subject to any disclaimer, the term of this patent is extended or adjusted under 35 U.S.C. 154(b) by 0 days.

(21) Appl. No.: 12/282,851

(22) PCT Filed: Mar. 13, 2007

(86) PCT No.: PCT/EP2007/052357
§ 371 (c)(1),
(2), (4) Date: Feb. 12, 2009

(87) PCT Pub. No.: WO2007/104763
PCT Pub. Date: Sep. 20, 2007

(65) Prior Publication Data
US 2009/0220992 A1 Sep. 3, 2009

Related U.S. Application Data

(60) Provisional application No. 60/782,119, filed on Mar. 14, 2006.

(51) Int. Cl.
*G01N 33/53* (2006.01)
*G01N 33/542* (2006.01)
*G01N 33/566* (2006.01)
*G01N 33/567* (2006.01)

(52) U.S. Cl. .......... 435/7.8; 435/7.9; 435/7.72; 435/7.1; 436/501; 436/503

(58) Field of Classification Search .................. None
See application file for complete search history.

(56) References Cited

FOREIGN PATENT DOCUMENTS
| WO | WO 02/081466 | 10/2002 |
|----|--------------|---------|
| WO | WO 2004/006838 | 1/2004 |
| WO | WO 2006/134056 | 12/2006 |

OTHER PUBLICATIONS

Abou-Sleiman et al., "Expanding Insights of Mitochondrial Dysfunction in Parkinson's Disease" Nat Rev Neurosci. Mar. 2006;7(3):207-219.
Aniento and Gruenberg "Subcellular Fractionation of Tissue Culture Cells" Curr. Protoc. Protein Sci., Wiley Chapter 4.3, 4.3.1-4.3.21, 1998.
Ausubel et al, "Short Protocols in Molecular Biology" Fourth Edition, Wiley, Chapter 11, Immunology, 11.1-11.30, 1999.
Bantscheff et al., "Quantitative chemical proteomics reveals mechanisms of action of clinical ABL kinase inhibitors" Nat Biotechnol. Sep. 2007;25(9):1035-1044. Epub Aug. 26, 2007.
Breinbauer et al., "Natural product guided compound library development" Curr Med Chem. Dec. 2002;9(23):2129-2145.
Castle, "Purification of Organelles from Mammalian Cells" Curr Protoc Protein Sci., Wiley Chapter 4.2, 4.2.1-4.2.57, 1998.
Cookson, "The biochemistry of Parkinson's disease" Annu Rev Biochem. 2005;74:29-52.
Edwards and Morrell "Solid-phase compound library synthesis in drug design and development" Curr Opin Drug Discov Devel. Jul. 2002;5(4):594-605.
Gloeckner et al., "The Parkinson disease causing LRRK2 mutation I2020T is associated with increased kinase activity" Hum Mol Genet. Jan. 15, 2006;15(2):223-232. Epub Dec. 1, 2005.
Goodnow, "Current practices in generation of small molecule new leads" J Cell Biochem Suppl. 2001;Suppl 37:13-21.
Greggio et al., "Kinase activity is required for the toxic effects of mutant LRRK2/dardarin" Neurobiol Dis. Aug. 2006;23(2):329-341. Epub Jun. 5, 2006.
Karwa and Mitra, "Sample Preparation Techniques in Analytical Chemistry" Chemical Analysis v. 162, Wiley 331-375, 2003.
Langer "New Methods of Drug Delivery" Science 249:1527-1533, 1990.
Mallari et al., "A generic high-throughput screening assay for kinases: Protein Kinase A as an example" J Biomol Screen. Apr. 2003;8(2):198-204.
Mann et al., "Analysis of proteins and proteomes by mass spectrometry" Annu Rev Biochem. 2001;70:437-473.
Merlot et al., "Fragment analysis in small molecule discovery" Curr Opin Drug Discov Devel. May 2002;5(3):391-399.
Pasian-Ruiz et al., "Cloning of the gene containing mutations that cause PARK8-linked Parkinson's disease" Neuron. Nov. 18, 2004;44(4):595-600.
Perkins et al., "Probability-based protein identification by searching sequence databases using mass spectrometry data" Electrophoresis. Dec. 1999;20(18):3551-3567.
Petty, "Overview of the Physical State of Proteins Within Cells" Current Protocols in Cell Biology, 5.1.1-5.1.10, 1998.
Rodems et al., "A FRET-based assay platform for ultra-high density drug screening of protein kinases and phosphatases" Assay Drug Dev Technol. Nov. 2002;1(1 Pt 1):9-19.
Schutz-Geschwendener et al., "Quantative, two-color Western blot detection with infrared fluorescence" May 2004, LI-COR Biosciences, 1-7.
Seethala and Menzel, "A fluorescence polarization competition immunoassay for tyrosine kinases" Anal Biochem. Jan. 15, 1998;255(2):257-262.
Seethala and Menzel, "A homogeneous, fluorescence polarization assay for src-family tyrosine kinases" Anal Biochem. Nov. 15, 1997;253(2):210-218.
Seethala, "Fluorescence polarization competition immunoassay for tyrosine kinases" Methods. Sep. 2000;22(1):61-70.
Shevchenko et al., "Mass spectrometric sequencing of proteins from silver-stained polyacrylamide gels" Anal Chem. Mar. 1, 1996;68(5):850-858. Smith et al., "Leucine-rich repeat kinase 2 (LRRK2) interacts with parkin, and mutant LRRK2 induces neuronal degeneration" Proc Natl Acad Sci U S A. Dec. 20, 2005;102(51):18676-18681. Epub Dec. 13, 2005.
Subramanian, "Immunoaffinity chromatography" Mol Biotechnol. Jan. 2002;20(1):41-47.
Sun et al., "Discovery of 5-[5-fluoro-2-oxo-1,2- dihydroindol-(3Z)-ylidenemethyl]-2,4- dimethyl-1H-pyrrole-3-carboxylic acid (2-diethylaminoethyl)amide, a novel tyrosine kinase inhibitor targeting vascular endothelial and platelet-derived growth factor receptor tyrosine kinase" J Med Chem. Mar. 27, 2003;46(7):1116-1119.

(Continued)

Primary Examiner — Olga N Chernyshev
(74) Attorney, Agent, or Firm — Kristina Bieker-Brady; Clark & Elbing LLP

(57) ABSTRACT

The invention features methods for the identification of leucine-rich kinase 2 (LRRK2) inhibitors using indol ligand 91. Generally, these methods include identifying compounds that compete with indol ligand 91 for binding to LRRK2.

26 Claims, 3 Drawing Sheets

OTHER PUBLICATIONS

Figure 1:
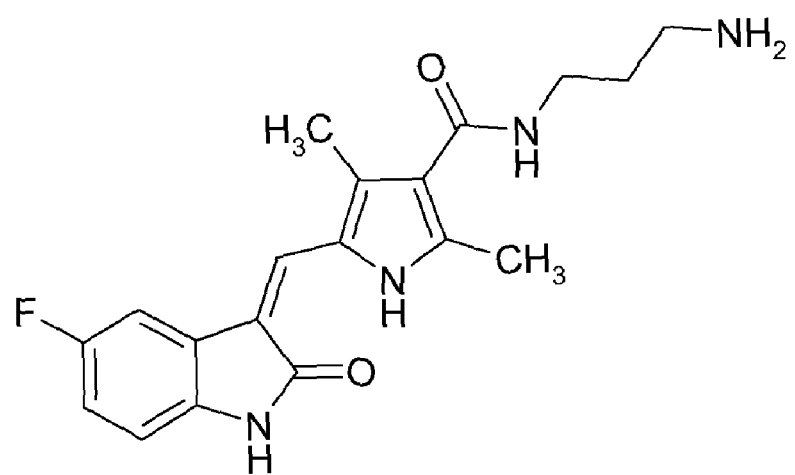

Taylor et al., "LRRK2: a common pathway for parkinsonism, pathogenesis and prevention?" Trends Mol Med. Feb. 2006;12(2):76-82. Epub Jan. 10, 2006.

Turek et al., "Development and validation of a competitive AKT serine/threonine kinase fluorescence polarization assay using a product-specific anti-phospho-serine antibody" Anal Biochem. Dec. 1, 2001;299(1):45-53.

Wakeling et al., "Specific inhibition of epidermal growth factor receptor tyrosine kinase by 4-anilinoquinazolines" Breast Cancer Res Treat. 1996;38(1):67-73.

Wingfield, "Production of Recombinant Proteins" Curr Protoc Protein Sci., Chapter 5, 5.01-5.03, 1995.

Wu and Wu, "Receptor-mediated in vitro gene transformation by a soluble DNA carrier system" J Biol Chem. Apr. 5, 1987;262(10):4429-4432.

Wu et al., "Comparative study of three proteomic quantitative methods, DIGE, cICAT, and iTRAQ, using 2D gel- or LC-MALDI TOF/TOF" J Proteome Res. Mar. 2006;5(3):651-658.

Wu et al., "Identification of a high-affinity anti-phosphoserine antibody for the development of a homogeneous fluorescence polarization assay of protein kinase C" J Biomol Screen. Feb. 2000;5(1):23-30.

Zhang et al., "Nocodazole-induced p53-dependent c-Jun N-terminal kinase activation reduces apoptosis in human colon carcinoma HCT116 cells" J Biol Chem. Nov. 15, 2002;277(46):43648-43658. Epub Sep. 6, 2002.

Zimprich et al., "Mutations in LRRK2 cause autosomal-dominant parkinsonism with pleomorphic pathology" Neuron. Nov. 18, 2004;44(4):601-607.

Dzamko et al., "Inhibition of LRRK2 kinase activity leads to dephosphorylation of Ser(910)/Ser(935), disruption of 14-3-3 binding and altered cytoplasmic localization" Biochem J. Aug. 27, 2010;430(3):405-413.

Liu et al., "Development of a mechanism-based high-throughput screen assay for leucine-rich repeat kinase 2—discovery of LRRK2 inhibitors" Anal Biochem. Sep. 15, 2010;404(2):186-192.

Pedro et al., "Development of a high-throughput AlphaScreen assay measuring full-length LRRK2(G2019S) kinase activity using moesin protein substrate" Anal Biochem. Sep. 1, 2010;404(1):45-51.

West et al., "Parkinson's disease-associated mutations in leucine-rich repeat kinase 2 augment kinase activity" Proc Natl Acad Sci U S A. Nov. 15, 2005;102(46):16842-16847.

Figure 3

```
   1 MASGACQGCE EEEEEEALKK LIVRLNNVQE GKQIETLLQL LEDMLVFTYS
  51 DRASKLFEDK NFHVPLLIVL DSYMRVASVQ QAGWSLLCKL IEVCPGTLQS
 101 LIGPQDIGND WEVLGIHRLI LKMLTVHHAN VNLSIVGLKA LDLLLDSGKL
 151 TLLILDEECD IFLLIFDAMH RYSANDEVQK LGCKALHVLF ERVSEEQLTE
 201 FVENKDYTIL LSTFGSFRRD KEIVYHVLCC LHSLAVTCSN VEVLMSGNVR
 251 CYNLVVEAMK AFPTNENIQE VSCSLFQKLT LGNFFNILVL NEVHVFVVKA
 301 VRQYPENAAL QISALSCLAL LTETIFLNQD LEERSETQEQ SEEEDSEKLF
 351 WLEPCYKALV RHRKDKHVQE AACWALNNLL MYQNSLHEKI GDEDGQFPAH
 401 REVMLSMLMH SSSKDVFQAA AHALSTLLEQ NVNFRKILLA KGVYLNVLEL
 451 MQKHAHAPEV AESGCKMLSH LFEGSNPSLD TMAAVVPKIL TVMKAHGTSL
 501 SVQLEALRAI LHFVVPGLLE ESREDSQCRP NVLRKQCFRT DIHKLVLVAL
 551 NRFIGNPGIQ KCGLKVISSL AHLPDATETL SLQGAVDSVL HTLQMYPDDQ
 601 EIQCLGLHLM GCLMTKKNFC IGTGHLLAKI LASTLQRFKD VAEVQTTGLQ
 651 TTLSILELSV SFSKLLVHYS FDVVIFHQMS SSVVEQKDEQ FLNLCCKCFA
 701 KVAVDDELKN TMLERACDQN NSIMVECLLL LGADANQVKG ATSLIYQVCE
 751 KESSPKLVEL LLNGGCREQD VRKALTISIQ KGDSQVISLL LRKLALDLAN
 801 NSICLGGFGI GKIDPSWLGP LFPDKSSNLR KQTNTGSVLA RKVLRYQMRN
 851 TLQEGVASGS DGNFSEDALA KFGEWTFIPD SSMDSVFGQS DDLDSEGSES
 901 SFLVKRKSNS ISVGEVYRDL ALQRYSPNAQ RHSNSLGPVF DHEDLLRRKR
 951 KILSSDESLR SSRLPSHMRQ SDSSSSLASE REHITSLDLS ANELKDIDAL
1001 SQKCCLSSHL EHLTKLELHQ NSLTSFPQQL CETLKCLIHL DLHSNKFTSF
1051 PSFVLKMPRI TNLDASRNDI GPTVVLDPAM KCPSLQLNL SYNQLSSIPE
1101 NLAQVVEKLE QLLLEGNKIS GICSPLSLKE LKILNLSKNH IPSLPGDFLE
1151 ACSKVESFSA RMNFLAAMPA LPSSITSLKL SQNSFTCIPE AIFSLPHLRS
1201 LDMSHNNIEC LPGPAHWKSL NLRELIFSKN QISTLDFSEN PHVWSRVEKL
1251 HLSHNKLKEI PPEIGCLENL TSLDVSYNLE LRSFPNEMGK LSKIWDLPLD
1301 GLHLNFDFKH VGCKAKDIIR FLQQRLKKAV PYNRMKLMIV GNTGSGKTTL
1351 LQQLMKMKKP ELGMQGATVG IDVRDWSIQI RGKRRKDLVL NVWDFAGREE
1401 FYSTHPHFMT QRALYLAVYD LSKGQAEVDA MKPWLFNIKA RASSSPVILV
1451 GTHLDVSDEK QRKACISKIT KELLNKRGFP TIRDYHFVNA TEESDALAKL
1501 RKTIINESLN FKIRDQPVVG QLIPDCYVEL EKIILSERKA VPTEFPVINR
1551 KHLLQLVNEH QLQLDENELP HAVHFLNESG VLLHFQDPAL QLSDLYFVEP
1601 KWLCKVMAQI LTVKVDGCLK HPKGIISRRD VEKFLSKKKR FPKNYMMQYF
1651 KLLEKFQIAL PIGEEYLLVP SSLSDHRPVI ELPHCENSEI IIRLYEMPYF
1701 PMGFWSRLIN RLLEISPFML SGRERALRPN RMYWRQGIYL NWSPEAYCLV
1751 GSEVLDNRPE SFLKITVPSC RKGCILLGRV VDHIDSLMEE WFPGLLEIDI
1801 CGEGETLLKK WALYSFNDGE EHQKILLDEL MKKAEEGDLL INPDQPRLTI
1851 PISQIAPDLI LADLPRNIML NNDELEFEEA PEFLLGDSF GSVYRAAYEG
1901 EEVAVKIFNK HTSLRLLRQE LVVLCHLHHP SLISLLAAGI RPRMLVMELA
1951 SKGSLDRLLQ QDKASLTRTL QHRIALHVAD GLRYLHSAMI IYRDLKPHNV
2001 LLFTLYPNAA IIAKIADYGI AQYCCRMGIK TSEGTPGFRA PEVARGNVIY
2051 NQQADVYSFG LLLHDIWTTG SRIMEGLRFP NEFDELAIQG KLPDPVKEYG
2101 CAPWPMVEKL ITKCLKENPQ ERPTSAQVFD ILNSAELICL MRHILIPKNI
2151 IVECMVATNL NSKSATLWLG CGNTEKGQLS LFDLNTERYS YEEVADSRIL
2201 CLALVHLAAE KESWVVCGTQ SGALLVINVE EETKRHTLEK MTDSVTCLHC
2251 NSLAKQSKQS NFLLVGTADG NLMIFEDKAV KCKGAAPLKT LHIGDVSTPL
2301 MCLSESLNSS ERHITWGGCG TKVFSFSNDF TIQKLIETKT NQLFSYAAFS
2351 DSNIIALAVD TALYIAKKNS PVVEVWDKKT EKLCELIDCV HFLKEVMVKL
2401 NKESKHQLSY SGRVKALCLQ KNTALWIGTG GGHILLLDLS TRRVIRTIHN
2451 FCDSVRAMAT AQLGSLKNVM LVLGYKRKST EGIQEQKEIQ SCLSIWDLNL
2501 PHEVQNLEKH IEVRTELADK MRKTSVE
```

METHODS FOR THE IDENTIFICATION OF LRRK2 INTERACTING MOLECULES

The present invention relates to methods for the identification of LRRK2 interacting molecules and for the purification of LRRK2 using indol ligand 91 as a ligand for LRRK2. Furthermore, the present invention relates to pharmaceutical compositions comprising said interacting molecules e.g. for the treatment of Parkinson's disease.

Parkinson's disease (PD) is a heterogeneous movement disorder characterized by the degeneration of dopaminergic neurons within the substancia nigra of the basal ganglia. It affects 2% of the population over 60 years.

Current therapeutic strategies for PD focus primarily on reducing the severity of its symptoms using dopaminergic medications (e.g. Levodopa/Carbidopa). Although providing benefit to patients, these medications display adverse side effects and may become ineffective after prolonged treatment (wearing off effect). None of these treatments addresses the underlying problem, the progressive loss of dopaminergic neurons.

Broadly, there are two clinicopathological components of PD. First, there is clinically defined parkinsonism, a syndromic term which comprises the cardinal features of the Parkinsonian movement disorder. These are a resting tremor, bradykinesia (slowness of movement), rigidity and postural instability, all problems in initiating or stopping movements. Their pathological correlate is the loss of dopaminergic neurons in the substancia nigra. Second, Parkinson's disease is marked postmortem by the presence of Lewy bodies and Lewy neurites in surviving neurons. These are intracellular aggregations of lipids and proteins including ubiquitin and alpha-synuclein. Pathological definitions of PD require the presence of alpha-synuclein-positive Lewy pathology in surviving nigral neurons, combined with nigral cell loss and intact striatal neurons (Cookson, 2005. Annual Reviews in Biochemistry 74, 29-52).

The alpha-synuclein-centric theory of protein aggregation has in recent years been complemented by the discovery of the proteins DJ1, PINK1 and OMI/HTRA2, all of which are associated with the mitochondria and have been implicated in cellular protection against oxidative damage (Abou-Sleiman et al., 2006. Nature Reviews Neuroscience 7, 207-219).

Genetic evidence has recently been presented that mutations of the Leucine-rich repeat kinase 2 (LRRK2, synonym Dardarin) cause autosomal dominant PD previously linked to the PARK8 locus. LRRK2 mutations are estimated to account for 5 to 6% of PD cases with a positive family history, and were also identified in sporadic cases. LRRK2 encodes a large multi-domain protein that consists of N-terminal leucine-rich repeats, a GTPase ROC/COR domain, a mitogen-activated protein kinase kinase kinase (MAPKKK) and C-terminal WD40 repeats (Paisan-Ruiz et al., 2004. Neuron 44, 595-600; Zimprich et al., 2004. Neuron 44, 601-607). Paisan-Ruz and colleagues named the protein product dardarin, derived from the Basque word "dardara" meaning tremor, but the protein was later renamed LRRK2.

Currently, little is known about LRRK2 function but preliminary observations have been made in in vitro overexpression systems. LRRK2 encodes a protein kinase and is capable of autophosphorylation (West et al., 2005. PNAS 102, 16842-16847, Gloeckner, et al., 2005. Hum. Mol. Genet. 15, 223-232). The publication West et al. describes the purification of recombinant LRRK2 with the help of a specific antibody. However, the amount of protein obtained was very small.

Significantly, three PD-associated LRRK2 mutations, two in the kinase domain (G2019S and I2020T) and one in the ROC/COR GTPase domain (R1441C) increase LRRK2 autophosphorylation, suggesting a dominant gain-of-function mechanism. Indeed, overexpression of R1441C, Y1699C or G2019S mutants of LRRK2 is sufficient to induce neuronal degeneration in mouse primary cortical neurons (Smith et al., 2005. PNAS 102, 18676-18681).

Moreover, manipulating the kinase activity of LRRK2 by replacing the kinase domain with a "kinase-dead" mutated version blocks the formation of inclusion bodies and delays cell death, two cellular phenotypes of PD (Greggio et al., 2006. Neurobiol. Dis. 23(2), 329-341). This observation suggests that kinase inhibitors will be useful therapeutic agents for patients with LRRK2 mutations and presumably also sporadic PD.

The recent discovery that LRRK2 mutations lead to late-onset PD with pleomorphic pathology, including alpha-synuclein, tau and ubiquitin pathology places LRRK2 upstream in a common neurodegenerative pathway for parkinsonism. Thus, LRRK2 has become an attractive therapeutic target for intervention and neuroprotection in Parkinson's disease (Taylor et al., 2006. Trends in Molecular Medicine 12, 76-82).

In view of the above, there is a need for providing effective methods for the identification of LRRK2 interacting compounds as well as for methods for the purification of LRRK2.

To comply with this need, the invention provides in a first aspect a method for the identification of an LRRK2 interacting compound, comprising the steps of
  a) providing a protein preparation containing LRRK2,
  b) contacting the protein preparation with indol ligand 91 immobilized on a solid support under conditions allowing the formation of an indol ligand 91-LRRK2 complex,
  c) incubating the indol ligand 91-LRRK2 complex with a given compound, and
  d) determining whether the compound is able to separate LRRK2 from the immobilized indol ligand 91.

Furthermore, in a second aspect, the invention relates to a method for the identification of an LRRK2 interacting compound, comprising the steps of
  a) providing a protein preparation containing LRRK2,
  b) contacting the protein preparation with indol ligand 91 immobilized on a solid support and with a given compound under conditions allowing the formation of an indol ligand 91-LRRK2 complex, and
  c) detecting the indol ligand 91-LRRK2 complex formed in steps b).

In a third, preferred aspect, the invention provides a method for the identification of an LRRK2 interacting compound, comprising the steps of:
  a) providing two aliquots of a protein preparation containing LRRK2,
  b) contacting one aliquot with indol ligand 91 immobilized on a solid support under conditions allowing the formation of an indol ligand 91-LRRK2 complex,
  c) contacting the other aliquot with indol ligand 91 immobilized on a solid support and with a given compound under conditions allowing the formation of an indol ligand 91-LRRK2 complex, and
  d) determining the amount of indol ligand 91-LRRK2 complex formed in steps b) and c).

In the context of the present invention, it has been surprisingly found that indol ligand 91 is a ligand for LRRK2. This enables the use of indol ligand 91 in screening assays, i.e. in competitive screening assays as well as in methods for the purification of LRRK2.

The structure of indol ligand 91, (5-[5-Fluoro-2-oxo-1,2-dihydro-indol-(3Z)-ylidenemethyl]-2,4-dimethyl-1H-pyrrole-3-carboxylic acid (3-amino-propyl)-amide), is given in FIG. 1. This compound is a molecule structurally similar to the kinase inhibitor Sutent (SU11248; Sun et al., 2003. J. Med. Chem. 46, 1116-1119). Indol ligand 91 can be covalently coupled to a suitable solid support material via the primary amino group and be used for the isolation of binding proteins. The synthesis of indol ligand 91 is described in Example 1. According to the invention, the expression "indol ligand 91" also includes compounds comprising the identical core but which have another linker, preferably coupled to the NH group not being part of the cyclic structures, for linkage to the solid support. Typically linkers may have a backbone of 8, 9 or 10 atoms and may contain either a carboxy- or amino-active group.

According to the present invention, the expression "LRRK2" does not only mean the protein as shown in FIG. 3 but also a functionally active derivative thereof, or a functionally active fragment thereof, or a homologue thereof, or a variant encoded by a nucleic acid that hybridizes to the nucleic acid encoding said protein under low stringency conditions. Preferably, these low stringency conditions include hybridization in a buffer comprising 35% formamide, 5×SSC, 50 mM Tris-HCl (pH 7.5), 5 mM EDTA, 0.02% PVP, 0.02% BSA, 100 ug/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1-5 hours at 55° C., and washing in a buffer consisting of 2×SSC, 25 mM Tris-HCl (pH 7.4) 5 mM EDTA, and 0.1% SDS for 1.5 hours at 60° C.

Moreover, according to the present invention, the expression "LRRK" includes mutant forms of LRRK2, preferably such mutant forms which observed in PD (in familial forms as well as sporadic cases). Mutations in the LRRK2 gene have been shown to cause familial autosomal dominant PD (West et al., 2005. PNAS 102, 16842-16847). More preferred, these mutant forms include single amino acid mutations.

The single amino acid substitution G2019S is one of the most frequently observed mutations Taylor et al, 2006. Trends in Molecular Medicine 12, 76-82). This mutation is located in the kinase domain within a conserved region of the activation loop suggesting that modulation of the kinase activity may be involved in the pathogenic mechanism. Other mutations observed in PD include R1441C, Y1699C, and I2020T (see Table 2 of Taylor et al.).

Therefore, in a preferred embodiment, the expression "LRRK2" also includes an LRRK2 protein having a G2019S, R1441C, Y1699C, or I2020T mutation. More preferably, the expression "LRRK2" also includes an LRKK2 protein having one of the following single mutations: G2019S, R1441C, Y1699C, or I2020T.

Furthermore, 15 additional putatively pathogenic amino acid substitutions have been identified in LRRK2 (Taylor et al, 2006. Trends in Molecular Medicine 12, 76-82, see especially FIG. 2).

Therefore, in a preferred embodiment, the expression "LRRK2" also includes an LRRK2 protein having a R793M, Q930R, R1067Q, S1096C, I1122V, S1228T, I1371V, R1441G, R1441H, R1514Q, M1869T, R1941H, I2012T, T2356I or G2385R mutation. More preferably, the expression "LRRK2" also includes an LRKK2 protein having one of the following single mutations: R793M, Q930R, R1067Q, S1096C, I1122V, S1228T, I1371V, R1441G, R1441H, R1514Q, M1869T, R1941H, I2012T, T2356I or G2385R.

In the methods of the invention, first a protein preparation containing LRRK2 is provided. The methods of the present invention can be performed with any protein preparation as a starting material, as long as the LRRK2 is solubilized in the preparation. Examples include a liquid mixture of several proteins, a partial cell lysate which contains not all proteins present in the original cell or a combination of several cell lysates.

Partial cell lysates can be obtained by isolating cell organelles (e.g. nucleus, mitochondria, ribosomes, golgi etc.) first and then preparing protein preparations derived from these organelles. Methods for the isolation of cell organelles are known in the art (Chapter 4.2 Purification of Organelles from Mammalian Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

In addition, protein preparations can be prepared by fractionation of cell extracts thereby enriching specific types of proteins such as cytoplasmic or membrane proteins (Chapter 4.3 Subcellular Fractionation of Tissue Culture Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

Furthermore protein preparations from body fluids can be used (e.g. blood, cerebrospinal fluid, peritoneal fluid and urine).

For example whole embryo lysates derived from defined development stages or adult stages of model organisms such as *C. elegans* can be used. In addition, whole organs such as heart dissected from mice can be the source of protein preparations. These organs can also be perfused in vitro in order to obtain a protein preparation.

Furthermore, the protein preparation may be a preparation containing LRRK2 which has been recombinantely produced. Methods for the production of recombinant proteins in prokaryotic and eukaryotic cells are widely established (Chapter 5 Production of Recombinant Proteins in "Current Protocols in Protein Science", Editors: John. E. Coligan, Ben M. Dunn, Hidde L. Ploegh, David W. Speicher, Paul T. Wingfield; Wiley, 1995, ISBN: 0-471-14098-8).

In a preferred embodiment of the methods of the invention, the provision of a protein preparation includes the steps of harvesting at least one cell containing LRRK2 and lysing the cell.

In a preferred embodiment, the cell is part of a cell culture system and methods for the harvest of a cell out of a cell culture system are known in the art (literature supra).

The choice of the cell will mainly depend on the expression of LRRK2, since it has to be ensured that the protein is principally present in the cell of choice. In order to determine whether a given cell is a suitable starting system for the methods of the invention, methods like Westernblot, PCR-based nucleic acids detection methods, Northernblots and DNA-microarray methods ("DNA chips") might be suitable in order to determine whether a given protein of interest is present in the cell.

The choice of the cell will also be influenced by the purpose of the study. If the in vivo efficacy for a given drug needs to be analyze then cells or tissues will be selected in which the desired therapeutic effect occurs (e.g. brain tissue for anti-neurodegenerative drugs). By contrast, for the elucidation of protein targets mediating unwanted side effects the cell or tissue will be analysed in which the side effect is observed (e.g. liver tissue for drug metabolism).

Furthermore, it is envisaged within the present invention that the cell containing LRRK2 may be obtained from an organism, e.g. by biopsy. Corresponding methods are known in the art. For example, a biopsy is a diagnostic procedure used to obtain a small amount of tissue, which can then be examined microscopically or with biochemical methods. Biopsies are important to diagnose, classify and stage a disease, but also to evaluate and monitor drug treatment.

It is encompassed within the present invention that by the harvest of the at least one cell, the lysis is performed simultaneously. However, it is equally preferred that the cell is first harvested and then separately lysed.

Methods for the lysis of cells are known in the art (Karwa and Mitra: Sample preparation for the extraction, isolation, and purification of Nuclei Acids; chapter 8 in "Sample Preparation Techniques in Analytical Chemistry", Wiley 2003, Editor: Somenath Mitra, print ISBN: 0471328456; online ISBN: 0471457817). Lysis of different cell types and tissues can be achieved by homogenizers (e.g. Potter-homogenizer), ultrasonic desintegrators, enzymatic lysis, detergents (e.g. NP-40, Triton X-100, CHAPS, SDS), osmotic shock, repeated freezing and thawing, or a combination of these methods.

According to the methods of the invention, the protein preparation is contacted with indol ligand 91 immobilized on a solid support under conditions allowing the formation of a indol ligand 91-LRRK2 complex.

In the present invention, the term "a indol ligand 91-LRRK2 complex" denotes a complex where indol ligand 91 interacts with LRRK2, e.g. by covalent or, most preferred, by non-covalent binding.

The skilled person will know which conditions can be applied in order to enable the formation of the indol ligand 91-LRRK2 complex.

In the context of the present invention, the term "under conditions allowing the formation of the complex" includes all conditions under which such formation, preferably such binding is possible. This includes the possibility of having the solid support on an immobilized phase and pouring the lysate onto it. In another preferred embodiment, it is also included that the solid support is in a particulate form and mixed with the cell lysate.

In the context of non-covalent binding, the binding between indol ligand 91 and LRRK2 is, e.g., via salt bridges, hydrogen bonds, hydrophobic interactions or a combination thereof.

In a preferred embodiment, the steps of the formation of the indol ligand 91-LRRK2 complex are performed under essentially physiological conditions. The physical state of proteins within cells is described in Petty, 1998 (Howard R. Petty, Chapter 1, Unit 1.5 in: Juan S. Bonifacino, Mary Dasso, Joe B. Harford, Jennifer Lippincott-Schwartz, and Kenneth M. Yamada (eds.) *Current Protocols in Cell Biology* Copyright© 2003 John Wiley & Sons, Inc. All rights reserved. DOI: 10.1002/0471143030.cb0101s00Online Posting Date May, 2001 Print Publication Date: October, 1998).

The contacting under essentially physiological conditions has the advantage that the interactions between the ligand, the cell preparation (i.e. the enzyme to be characterized) and optionally the compound reflect as much as possible the natural conditions. "Essentially physiological conditions" are inter alia those conditions which are present in the original, unprocessed sample material. They include the physiological protein concentration, pH, salt concentration, buffer capacity and post-translational modifications of the proteins involved. The term "essentially physiological conditions" does not require conditions identical to those in the original living organism, wherefrom the sample is derived, but essentially cell-like conditions or conditions close to cellular conditions. The person skilled in the art will, of course, realize that certain constraints may arise due to the experimental set-up which will eventually lead to less cell-like conditions. For example, the eventually necessary disruption of cell walls or cell membranes when taking and processing a sample from a living organism may require conditions which are not identical to the physiological conditions found in the organism. Suitable variations of physiological conditions for practicing the methods of the invention will be apparent to those skilled in the art and are encompassed by the term "essentially physiological conditions" as used herein. In summary, it is to be understood that the term "essentially physiological conditions" relates to conditions close to physiological conditions, as e.g. found in natural cells, but does not necessarily require that these conditions are identical.

Preferably, "essentially physiological conditions" may comprise 50-200 mM NaCl or KCl, pH 6.5-8.5, 20-45° C., and 0.001-10 mM divalent cation (e.g. Mg++, Ca++); more preferably about 150 m NaCl or KCl, pH7.2 to 7.6, 5 mM divalent cation and often include 0.01-1.0 percent non-specific protein (e.g. BSA). A non-ionic detergent (Tween, NP-40, Triton-X100) can often be present, usually at about 0.001 to 2%, typically 0.05-0.2% (volume/volume). For general guidance, the following buffered aqueous conditions may be applicable: 10-250 mM NaCl, 5-50 mM Tris HCl, pH5-8, with optional addition of divalent cation(s) and/or metal chelators and/or non-ionic detergents.

In the context of the present invention, indol ligand 91 is immobilized on a solid support. Throughout the invention, the term "solid support" relates to every undissolved support being able to immobilize a small molecule ligand on its surface.

According to a further preferred embodiment, the solid support is selected from the group consisting of agarose, modified agarose, sepharose beads (e.g. NHS-activated sepharose), latex, cellulose, and ferro- or ferromagnetic particles.

Indol ligand 91 may be coupled to the solid support either covalently or non-covalently. Non-covalent binding includes binding via biotin affinity ligands binding to steptavidin matrices.

Preferably, indol ligand 91 is covalently coupled to the solid support.

Before the coupling, the matrixes can contain active groups such as NHS, Carbodimide etc. to enable the coupling reaction with indol ligand 91. indol ligand 91 can be coupled to the solid support by direct coupling (e.g. using functional groups such as amino-, sulfhydryl-, carboxyl-, hydroxyl-, aldehyde-, and ketone groups) and by indirect coupling (e.g. via biotin, biotin being covalently attached to indol ligand 91 and non-covalent binding of biotin to streptavidin which is bound to solid support directly).

The linkage to the solid support material may involve cleavable and non-cleavable linkers. The cleavage may be achieved by enzymatic cleavage or treatment with suitable chemical methods.

Preferred binding interfaces for binding indol ligand 91 to solid support material are linkers with a C-atom backbone. Typically linkers have backbone of 8, 9 or 10 atoms. Equally preferred are polyethylenglycol (PEG) linkers.

The skilled person will appreciate that between the individual steps of the methods of the invention, washing steps may be necessary. Such washing is part of the knowledge of the person skilled in the art. The washing serves to remove non-bound components of the cell lysate from the solid support. Nonspecific (e.g. simple ionic) binding interactions can be minimized by adding low levels of detergent or by moderate adjustments to salt concentrations in the wash buffer.

According to the identification methods of the invention, the read-out system is either the detection or determination of LRRK2 (first aspect of the invention), the detection of the indol ligand 91-LRRK2 complex (second aspect of the invention), the determination of the amount of the indol ligand 91-LRRK2 complex (third aspect of the invention).

The detection of the indol ligand 91-LRRK2 complex according to the second aspect of the invention can be performed by using labeled antibodies directed against LRRK2 and a suitable readout system.

Antibodies directed against LRRK2 and methods of their use are known in the art, also methods for labeling of antibodies (for example with fluorescent dyes). Anti-LRRK2 antibodies are commercially available (Santa Cruz Biotechnology Inc., Santa Cruz, Calif., USA). In addition, antibodies directed at mutated forms of LRRK2 (for example the G2019S and I2020T amino acid substitutions observed in familial forms of PD) are commercially available (Abgent, San Diego, Calif., USA).

However, in the course of the second and third aspect of the invention, it is preferred that LRRK2 is separated from the immobilized indol ligand 91.

According to the invention, separating means every action which destroys the interactions between indol ligand 91 and LRRK2. This includes in a preferred embodiment the elution of LRRK2 from the immobilized indol ligand 91.

The elution can be achieved by using non-specific reagents as described in detail below (ionic strength, pH value, detergents). In addition, it can be tested whether a compound of interest can specifically elute LRRK2. Such LRRK2 interacting compounds are described further in the following sections.

Such non-specific methods for destroying the interaction are principally known in the art and depend on the nature of the ligand enzyme interaction. Principally, change of ionic strength, the pH value, the temperature or incubation with detergents are suitable methods to dissociate the target enzymes from the immobilized ligand. The application of an elution buffer can dissociate binding partners by extremes of pH value (high or low pH; e.g. lowering pH by using 0.1 M citrate, pH2-3), change of ionic strength (e.g. high salt concentration using NaI, KI, MgCl2, or KCl), polarity reducing agents which disrupt hydrophobic interactions (e.g. dioxane or ethylene glycol), or denaturing agents (chaotropic salts or detergents such as Sodium-docedyl-sulfate, SDS; Review: Subramanian A., 2002, Immunoaffinity chromatography).

In some cases, the solid support has preferably to be separated from the released material. The individual methods for this depend on the nature of the solid support and are known in the art. If the support material is contained within a column the released material can be collected as column flowthrough. In case the support material is mixed with the lysate components (so called batch procedure) an additional separation step such as gentle centrifugation may be necessary and the released material is collected as supernatant. Alternatively magnetic beads can be used as solid support so that the beads can be eliminated from the sample by using a magnetic device.

In step d) of the method according to the first aspect of the invention, it is determined if LRRK2 has been separated from immobilized LRRK2. This may include the detection of LRRK2 or the determination of the amount of LRRK2.

Consequently, in preferred embodiments of all identification methods of the invention, methods for the detection of LRRK2 or for the determination of its amount are used. Such methods are known in the art and include physico-chemical methods such as protein sequencing (e.g. Edmann degradation), analysis by mass spectrometry methods or immunodetection methods employing antibodies directed against LRRK2.

Preferably, LRRK2 is detected or the amount of LRRK2 is determined by mass spectrometry or immunodetection methods.

The identification of proteins with mass spectrometric analysis (mass spectrometry) is known in the art (Shevchenko et al., 1996, Analytical Chemistry 68: 850-858; Mann et al., 2001, Analysis of proteins and proteomes by mass spectrometry, Annual Review of Biochemistry 70, 437-473) and is further illustrated in the example section.

Preferably, the mass spectrometry analysis is performed in a quantitative manner, for example by using iTRAQ technology (isobaric tags for relative and absolute quantification) or cICAT (cleavable isotope-coded affinity tags) (Wu et al., 2006. J. Proteome Res. 5, 651-658).

According to a further preferred embodiment of the present invention, the characterization by mass spectrometry (MS) is performed by the identification of proteotypic peptides of LRRK2. The concept of proteotypic peptides is described in detail in the example section. The idea is that LRRK2 is digested with proteases and the resulting peptides are determined by MS. As a result, peptide frequencies for peptides from the same source protein differ by a great degree, the most frequently observed peptides that "typically" contribute to the identification of this protein being termed "proteotypic peptide". Therefore, a proteotypic peptide as used in the present invention is an experimentally well observable peptide that uniquely identifies a specific protein or protein isoform.

According to a preferred embodiment, the characterization is performed by comparing the proteotypic peptides obtained in the course of practicing the methods of the invention with known proteotypic peptides. Since, when using fragments prepared by protease digestion for the identification of a protein in MS, usually the same proteotypic peptides are observed for a given enzyme, it is possible to compare the proteotypic peptides obtained for a given sample with the proteotypic peptides already known for enzymes of a given class of enzymes and thereby identifying the enzyme being present in the sample.

As an alternative to mass spectrometry analysis, the eluted LRRK2 (including coeluted binding partners or scaffold proteins), can be detected by using specific antibodies directed against LRRK2.

Furthermore, in another preferred embodiment, once the identity of the coeluted binding partner has been established by mass spectrometry analysis, each binding partner can be detected with specific antibodies directed against this protein.

Suitable antibody-based assays include but are not limited to Western blots, ELISA assays, sandwich ELISA assays and antibody arrays or a combination thereof. The establishment of such assays is known in the art (Chapter 11, Immunology, pages 11-1 to 11-30 in: Short Protocols in Molecular Biology. Fourth Edition, Edited by F. M. Ausubel et al., Wiley, New York, 1999).

These assays can not only be configured in a way to detect and quantify an enzyme of interest, but also to analyse post-translational modification patterns such as phosphorylation. For example, the activation state of a kinase can be determined by probing its phosphorylation status with specific anti-phosphotyrosine, anti-phosphoserine or anti-phosphothreonine antibodies. It is known in the art how to select and use such anti-phospho antibodies (Zhang et al., 2002. Journal of Biological Chemistry 277, 43648-43658).

Furthermore, the identification methods of the invention involve the use of compounds which are tested for their ability to be an LRRK2 interacting compound.

Principally, according to the present invention, such a compound can be every molecule which is able to interact with LRRK2. Preferably, the compound has an effect on LRRK2, e.g. a stimulatory, activating or inhibitory effect.

Preferably, said compound is selected from the group consisting of synthetic or naturally occurring chemical compounds or organic synthetic drugs, more preferably small molecules, organic drugs or natural small molecule compounds. Preferably, said compound is identified starting from a library containing such compounds. Then, in the course of the present invention, such a library is screened.

Such small molecules are preferably not proteins or nucleic acids. Preferably, small molecules exhibit a molecular weight of less than 1000 Da, more preferred less than 750 Da, most preferred less than 500 Da.

A "library" according to the present invention relates to a (mostly large) collection of (numerous) different chemical entities that are provided in a sorted manner that enables both a fast functional analysis (screening) of the different individual entities, and at the same time provide for a rapid identification of the individual entities that form the library. Examples are collections of tubes or wells or spots on surfaces that contain chemical compounds that can be added into reactions with one or more defined potentially interacting partners in a high-throughput fashion. After the identification of a desired "positive" interaction of both partners, the respective compound can be rapidly identified due to the library construction. Libraries of synthetic and natural origins can either be purchased or designed by the skilled artisan.

Examples of the construction of libraries are provided in, for example, Breinbauer R, Manger M, Scheck M, Waldmann H. Natural product guided compound library development. Curr Med. Chem. 2002 December; 9(23):2129-45, wherein natural products are described that are biologically validated starting points for the design of combinatorial libraries, as they have a proven record of biological relevance. This special role of natural products in medicinal chemistry and chemical biology can be interpreted in the light of new insights about the domain architecture of proteins gained by structural biology and bioinformatics. In order to fulfill the specific requirements of the individual binding pocket within a domain family it may be necessary to optimise the natural product structure by chemical variation. Solid-phase chemistry is said to become an efficient tool for this optimisation process, and recent advances in this field are highlighted in this review article. Other related references include Edwards P J, Morrell A I. Solid-phase compound library synthesis in drug design and development. Curr Opin Drug Discov Devel. 2002 July; 5(4):594-605; Merlot C, Domine D, Church D J. Fragment analysis in small molecule discovery. Curr Opin Drug Discov Devel. 2002 May; 5(3):391-9. Review; Goodnow R A Jr. Current practices in generation of small molecule new leads. J Cell Biochem Suppl. 2001; Suppl 37:13-21; which describes that the current drug discovery processes in many pharmaceutical companies require large and growing collections of high quality lead structures for use in high throughput screening assays. Collections of small molecules with diverse structures and "drug-like" properties have, in the past, been acquired by several means: by archive of previous internal lead optimisation efforts, by purchase from compound vendors, and by union of separate collections following company mergers. Although high throughput/combinatorial chemistry is described as being an important component in the process of new lead generation, the selection of library designs for synthesis and the subsequent design of library members has evolved to a new level of challenge and importance. The potential benefits of screening multiple small molecule compound library designs against multiple biological targets offers substantial opportunity to discover new lead structures.

In a preferred embodiment of the second aspect of the invention, LRRK2 is first incubated with the compound and then with the immobilized indol ligand 91. However, the simultaneous incubation of the compound and the immobilized indol ligand 91 (coincubation) with the LRRK2 containing protein is equally preferred (competitive binding assay).

Preferably the LRRK2 is first incubated with the compound for 10 to 60 minutes, more preferred 30 to 45 minutes at a temperature of 4° C. to 37° C., more preferred 4° C. to 25° C., most preferred 4° C. Preferably compounds are used at concentrations ranging from 1 µM to 1 mM, preferably from 10 to 100 µM. The second step, contacting with the immobilized ligand, is preferably performed for 10 to 60 minutes at 4° C.

In the case of simultaneous incubation, the LRRK2 is preferably simultaneously incubated with the compound and immobilized indol ligand 91 for 10 to 120 minutes, more preferred 20 to 60 minutes at a temperature of 4° C. to 37° C., more preferred 4° C. to 25° C., most preferred 4° C. to 8° C. Preferably compounds are used at concentrations ranging from 1 nM to 100 µM, preferably from 10 nM to 10 µM.

Furthermore, steps a) to c) of the second aspect of the invention may be performed with several protein preparations in order to test different compounds. This embodiment is especially interesting in the context of medium or high throughput screenings (see below).

In a preferred embodiment of the method of the invention according to the third aspect, a reduced amount of indol ligand 91-LRRK2 formed in step c) in comparison to step b) indicates that LRRK2 is a target of the compound. This results from the fact that in step c) of this method of the invention, the compound competes with the ligand for the binding of LRRK2. If less LRRK2 is present in the aliquot incubated with the compound, this means preferably that the compound has competed with the inhibitor for the interaction with the enzyme and is, therefore, a direct target of the enzyme and vice versa.

Preferably, the identification methods of the invention are performed as a medium or high throughput screening. Such assays are known to the person skilled in the art (Mallari et al., 2003, A generic high-throughput screening assay for kinases: protein kinase A as an example, Journal of Biomolecular Screening 8, 198-204; Rodems et al., 2002, A FRET-based assay platform for ultra-high density screening of protein kinases and phosphatases, Assay and Drug Development Technologies 1 (1PT1), 9-19).

The interaction compound identified according to the present invention may be further characterized by determining whether it has an effect on LRRK2 activity, for example on its kinase activity (West et al., 2005. PNAS 102, 16842-16847). Such assays are known in the art, also in a format that allows medium to high throughput screening.

Briefly, a fluorescein-labeled peptide substrate may be incubated with the tyrosine kinase (e.g. LRRK2), ATP and an anti-phosphotyrosine antibody. As the reaction proceeds, the phosphorylated peptide binds to the anti-phosphotyrosine antibody, resulting in an increase in the polarization signal. Compounds that inhibit the kinase result in a low polarization signal.

Alternatively, the assay can be configured in a modified indirect format. A fluorescent phosphopeptide is used as a tracer for complex formation with the anti-phospho-tyrosine antibody yielding a high polarization signal. When unlabeled substrate is phosphorylated by the kinase, the product competes with the fluorescent phosphorylated peptide for the antibody. The fluorescent peptide is then released from the antibody into solution resulting in a loss of polarization signal. Both the direct and indirect assays can be used to identify inhibitors of protein tyrosine kinase activity (Seethala, 2000, Methods 22, 61-70; Seethala and Menzel, 1997, Anal. Biochem. 253, 210-218; Seethala and Menzel, 1998, Anal. Biochem. 255, 257-262).

This fluorescence polarization assay can be adapted for the use with protein serine/threonine kinases by replacing the antiphophotyrosine antibody with an anti-phosphoserine or anti-phosphothreonine antibody (Turek et al., 2001, Anal. Biochem. 299, 45-53, PMID 11726183; Wu et al., 2000, J. Biomol. Screen. 5, 23-30, PMID 10841597).

The compounds identified according to the present invention may further be optimized (lead optimisation). This subsequent optimisation of such compounds is often accelerated because of the structure-activity relationship (SAR) information encoded in these lead generation libraries. Lead optimisation is often facilitated due to the ready applicability of high-throughput chemistry (HTC) methods for follow-up synthesis.

One example of such a library and lead optimization is described in Wakeling A E, Barker A J, Davies D H, Brown D S, Green L R, Cartlidge S A, Woodburn J R. Specific inhibition of epidermal growth factor receptor tyrosine kinase by 4-anilinoquinazolines. Breast Cancer Res Treat. 1996; 38(1): 67-73.

The invention further relates to a method for the preparation of a pharmaceutical composition comprising the steps of
- a) identifying a LRRK2 interacting compound as described above, and
- b) formulating the interacting compound to a pharmaceutical composition.

Therefore, the invention provides a method for the preparation of pharmaceutical compositions, which may be administered to a subject in an effective amount. In a preferred aspect, the therapeutic is substantially purified. The subject to be treated is preferably an animal including, but not limited to animals such as cows, pigs, horses, chickens, cats, dogs, etc., and is preferably a mammal, and most preferably human. In a specific embodiment, a non-human mammal is the subject.

In general, the pharmaceutical compositions of the present invention comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

The amount of the therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In general, suppositories may contain active ingredient in the range of 0.5% to 10% by weight; oral formulations preferably contain 10% to 95% active ingredient.

Various delivery systems are known and can be used to administer a therapeutic of the invention, e.g., encapsulation in liposomes, microparticles, and microcapsules: use of recombinant cells capable of expressing the therapeutic, use of receptor-mediated endocytosis (e.g., Wu and Wu, 1987, J. Biol. Chem. 262:4429-4432); construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (Langer, 1990, Science 249:1527-1533).

In yet another embodiment, the therapeutic can be delivered via a controlled release system. In one embodiment, a pump may be used (Langer, supra). In yet another embodiment, a controlled release system can be placed in proximity of the therapeutic target, i.e., the brain, thus requiring only a fraction of the systemic dose The invention further relates to a method for the purification of LRRK2, comprising the steps of
a) providing a protein preparation containing LRRK2,
b) contacting the protein preparation with indol ligand 91 immobilized on a solid support under conditions allowing the formation of an indol ligand 91-LRRK2 complex, and
c) separating LRRK2 from the immobilized indol ligand 91.

As mentioned above, it has been surprisingly found that indol ligand 91 is an LRRK2 ligand. This enables efficient LRRK2 purification methods.

With respect to LRRK2, the protein preparation containing LRRK2, the conditions for contacting with indol ligand 91, immobilized indol ligand 91, the indol ligand 91-LRRK2 complex, the separation of LRRK2 from the immobilized indol ligand 91, and the detection of LRRK2 or the determination of its amount, the embodiments as defined above for the identification methods of the invention also apply to the purification method of the invention.

In a preferred embodiment, the purification method of the invention further comprises after step c) the identification of proteins being capable of binding to LRRK2. This is especially interesting when the formation of the complex is performed under essentially physiological conditions, because it is then possible to preserve the natural condition of the enzyme which includes the existence of binding partners, enzyme subunits or post-translational modifications, which can then be identified with the help of mass spectrometry (MS).

Consequently, in a preferred embodiment, the purification method of the invention further comprises after step c) the determination whether LRRK2 is posttranslationally modified.

The invention further relates to the use of indol ligand 91 for the identification of LRRK2 interacting compounds and for the purification of LRRK-2. The embodiments as defined above also apply to the uses of the invention.

The invention is further illustrated by the following figures and examples, which are not considered as being limiting for the scope of protection conferred by the claims of the present application.

SHORT DESCRIPTION OF THE FIGURES

FIG. 1: Structure of linkable indol ligand 91
The figure shows the structure of linkable indol ligand 91. The free primary amino group can be used for covalent coupling to a solid support material.

Figure 2:
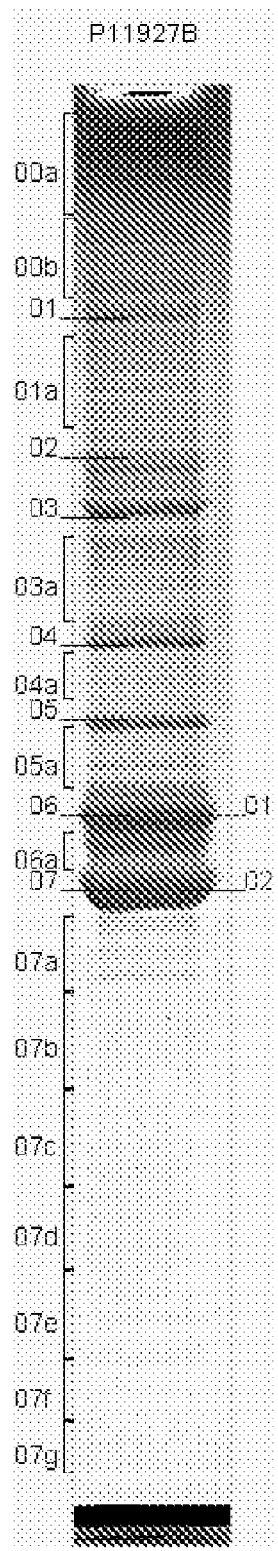

FIG. 2: Drug pulldown experiment with immobilized indol ligand 91
The figure shows the picture of a protein gel after staining with Coomassie blue. Proteins bound to immobilized indol ligand 91 were eluted with SDS sample buffer and analyzed by SDS-polyacrylamide gel electrophoresis (SDS-PAGE). The indicated gel areas were cut out as gel slices and proteins were subjected to analysis by mass spectrometry. The position of the band containing LRRK2 is in sample 01 in the upper part of the gel between 00b and 01a.

FIG. 3:
Peptides identified of LRRK2 The peptides that were identified by mass spectrometry analysis of the mouse LRRK2 sequence (IPI00227565.2, 2527 amino acids; SEQ ID NO:1) are underlined.

EXAMPLE 1

Synthesis of Linkable Indol Ligand 91

Synthesis of Indol Ligand 91

5-[5-Fluoro-2-oxo-1,2-dihydro-indol-(3Z)-ylidenemethyl]-2,4-dimethyl-1H-pyrrole-3-carboxylic acid (3-amino-propyl)-amide Step 1: 5-Fluoro-1,3-dihydro-indol-2-one A solution of 5-Fluoroisatin (1 g) in Hydrazine hydrate (55%, 10 ml) was heated at 110° C. for 30 minutes. Once the suspension has gone into solution, the reaction was heated at 110° C. for 4 hours, then cooled at 0° C. The precipitate was filtered and washed with water. The solid was suspended in water (10 ml), the pH was lowered to pH2 by addition of HCl conc, and the solution stirred at room temperature for 5 hours. The precipitate was collected, the solid washed with water (2×15 ml) and dried in the vacuum oven at 40° C. (0.26 g, 30%). $^1$H NMR (400 MHz, DMSO-$d_6$) δ 10.2 (s, 1H); 6.8-7.0 (dd, 2H); 6.6 (m, 1H); 3.2 (s, 2H); LCMS: method D, RT=1.736 min, [MH$^+$=152].

Step 2: {3-[(5-Formyl-2,4-dimethyl-1H-pyrrole-3-carbonyl)-amino]-propyl}-carbamic acid tert-butyl ester To a solution of 5-formyl-2,4-dimethyl-1H-pyrazol-3-carboxylic acid (0.300 g, 1.79 mmol), N-(3-Dimethylaminopropyl)-N'-ethylcarbodiimide (0.516 g, 2.69 mmol), 1-Hydroxybenzotriazole hydrate (0.364 g, 2.69 mmol), triethylamine (0.502 ml, 3.56 mmol) in dimethylformamide (3 ml) was added N-Boc-1,3-diaminopropane (0.375 ml, 2.15 mmol). The solution was stirred at room temperature for 15 hours. A mixture of brine (1.5 ml), water (1.5 ml) and saturated aqueous sodium bicarbonate (1.5 ml) was added and the pH of the solution adjusted to 12 by addition of 10N sodium hydroxide. The solution was extracted 3 times with a mixture of dichloromethane:Methanol (9:1). The organic layer was dried with anhydrous magnesium sulfate. The solvent was removed and the residue purified by flash chromatography (Hexane:Ethyl acetate (50 to 100%)) to yield the desired compound as a yellow solid (0.30 g, 52%). $^1$H NMR (400 MHz, DMSO-$d_6$) δ 11.90 (s, 1H); 9.50 (s, 1H); 7.50 (m, 1H); 6.90 (m, 1H); 3.20 (q, 2H); 3.00 (q, 2H); 2.30 (s, 3H)); 2.20 (s, 3H)); 1.60 (m, 2H)); 1.40 (s, 9H). LCMS: method D, RT=2.103 min, [M+Na$^+$=346], and [M−Boc+Na$^+$=246].

Step 3: [3-({5-[5-Fluoro-2-oxo-1,2-dihydro-indol-(3Z)-ylidenemethyl]-2,4-dimethyl-1H-pyrrole-3-carbonyl}-amino)-propyl]-carbamic acid tert-butyl ester A solution of {3-[(5-Formyl-2,4-dimethyl-1H-pyrrole-3-carbonyl)-amino]-propyl}-carbamic acid tert-butyl ester (0.200 g, 0.62 mmol) and 5-Fluoro-1,3-dihydro-indol-2-one (0.011 g, 0.62 mmol), pyrrolidine (0.003 ml) in ethanol (2 ml) was heated at 78° C. for 3 hours. The reaction was cooled to 0° C. and the resulting precipitate filtered, washed with cold ethanol. The product was suspended in ethanol (4 ml) and stirred at 72° C. for 30 minutes. The reaction was filtered, the precipitate dried in a vacuum oven at 40° C. to yield the desired compound as a solid (0.265 g, 94%). $^1$H NMR (400 MHz, DMSO-$d_6$) δ 13.8 (s, 1H); 11.00 (s, 1H); 7.80 (m, 2H); 7.70 (m, 1H); 7.0 (m, 1H); 6.9 (m, 2H); 3.30 (q, 2H); 3.10 (q, 2H); 2.50 (dd, 6H) 1.60 (m, 2H)); 1.40 (s, 9H). LCMS: method D, RT=2.86 min, [M+Na$^+$=479], and [M−Boc+Na$^+$=379].

Step 4: 5-[5-Fluoro-2-oxo-1,2-dihydro-indol-(3Z)-ylidenemethyl]-2,4-dimethyl-1H-pyrrole-3-carboxylic acid (3-amino-propyl)-amide

[3-({5-[5-Fluoro-2-oxo-1,2-dihydro-indol-(3Z)-ylidenemethyl]-2,4-dimethyl-1H-pyrrole-3-carbonyl}-amino)-propyl]-carbamic acid tert-butyl ester was suspended in methanol. 2 ml of HCl (4N) in dioxane was added and the reaction stirred at room temperature overnight. The solvent was removed to yield the desired compound (0.098 g, 91%). $^1$H NMR (400 MHz, DMSO-$d_6$) δ 13.8 (s, 1H); 11.00 (s, 1H); 7.90-7.70 (m, 5H); 6.9 (m, 2H); 3.30 (q, 2H); 2.80 (q, 2H); 2.50 (dd, 6H) 1.80 (m, 2H). LCMS: inconclusive due to fluorescence.

All reactions were carried out under inert atmosphere. NMR spectra were obtained on a Bruker dpx400. LCMS was carried out on an Agilent 1100 using a zorbax SBC-18, 4.6 mm×150 mm-5μ column or a Small column: ZORBAX® SB-C18, 4.6×75 mm, 3.5 microns ("short column"). Column flow was 1 ml/min and solvents used were water and acetonitrile (0.1% TFA) with an injection volume of 10 ul. Wavelengths were 254 and 210 nm. Methods are described below.

TABLE 1

Analytical methods

| Method | Easy Access Method Name | ChemStation Method Name | Flow Rate | Solvent | Run Time |
|---|---|---|---|---|---|
| A | Analytical positive 7mn | ANL_POS7.M | 1 ml/min | 0-2.5 min 5-95% MeCN 2.5-6 min 95% MeCN | 7 min |
| B | Analytical positive Ion | ANAL_POS.M | 1 ml/min | 0-11 min 5-95% MeCN 11-13 min 95% MeCN | 15 min |
| C | Loop injection, Positive | | 1 ml/min | 95% MeCN | 1 min |
| D | Analytical positive Ion | Short column ANL Positive | 1 ml/mn | 0-4.5 min 30-95% MeCN | 5 min |
| E | Analytical High pH | Analytical High pH | 3 ml/min | 0 to 8 min 5-95% MeCN 8 to 9 min 95% MeCN | 10 min |

TABLE 2

| Abbreviations used in chemistry protocols | |
|---|---|
| aq | aqueous |
| D | doublet |
| DMSO | dimethyl sulfoxide |
| G | gram |
| HCl | Hydrochloric acid |
| HPLC | high pressure liquid chromatography |
| LCMS | liquid chromatography - mass spectrometry |
| M | multiplet |
| mins | minute |
| mmol | millimole |
| N | Normal |
| NMR | nuclear magnetic resonance |
| Q | quartet |
| RT | retention time |
| S | singlet |
| sat | saturated |
| T | triplet |

EXAMPLE 2

Drug Pulldown with Immobilized Indol Ligand 91 and Identification of LRRK2

This example demonstrates the use of the immobilized indol ligand 91 ligand for the identification of LRRK2 from mouse brain lysate. Proteins binding to immobilized indol ligand 91 were identified using a chemical proteomics procedure. Binding proteins were purified on a resin to which indol ligand 91 was covalently attached. Bound proteins were eluted and subsequently separated by SDS-Polyacrylamide gel elecrophoresis (see FIG. 2), suitable gel bands were cut out and proteins were analyzed by LC-MS/MS mass spectrometry.

The results show that immobilized indol ligand 91 can be used to enrich and characterize LRRK2 from mouse brain lysates. The twelve LRRK2 peptides identified by mass spectrometry are listed in Table 4.

1. Immobilization of Small Molecule Amine Compounds

NHS-activated Sepharose 4 Fast Flow (Amersham Biosciences, 17-0906-01) was equilibrated with anhydrous DMSO (Dimethylsulfoxid, Fluka, 41648, H20<=0.005%). 1 ml of settled beads were placed in a 15 ml Falcon tube, compound stock solution (usually 100 mM in DMF or DMSO) was added (final conc. 0.2-2 µmol/ml beads) as well as 15 µl of TEA. Beads were incubated at room temperature in darkness on an end-over-end shaker (Roto Shake Genie, Scientific Industries Inc.) for 16-20 hours. Coupling efficiency was determined by HPLC. Non-reacted NHS-groups were blocked by incubation with aminoethanol at room temperature on the end-over-end shaker over night. Beads were washed with 10 ml of DMSO. Washed beads were stored in isopropanol at 4° C.

2. Preparation of Cell Lysates

Mouse brain tissue was homogenized in a Potter S homogenizer (5 ml per brain): 50 mM Tris-HCl, 1% CHAPSO, 5% glycerol, 150 mM NaCl, 1.5 mM MgCl2, 25 mM NaF, 1 mM sodium vanadate, 1 mM DTT, pH 7.5. One complete EDTA-free tablet (protease inhibitor cocktail, Roche Diagnostics, 1 873 580) per 25 ml buffer was added. The material was dounced 10× using a mechanized POTTER S, transferred to 50 ml falcon tubes, incubated for 30 minutes on ice and spun down for 10 min at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

3. Compound Pull-Down Experiment

Sepharose-beads with immobilized compound (100 µl beads per pull-down experiment) were equilibrated in lysis buffer and incubated with a cell lysate sample containing 50 mg of protein on an end-over-end shaker (Roto Shake Genie, Scientific Industries Inc.) for 2 hours at 4° C. Beads were collected, transferred to Mobicol-columns (MoBiTech 10055) and washed with 10 ml lysis buffer containing 0.5% detergent (NP40), followed by 5 ml lysis buffer with 0.25% detergent. To elute the bound protein, 60 µl 2×SDS sample buffer was added, the column was heated for 30 minutes at 50° C. and the eluate was transferred to a microfuge tube by centrifugation. Proteins were then separated by SDS-Polyacrylamide electrophoresis (SDS-PAGE).

4. Protein Identification by Mass Spectrometry 4.1 Protein Digestion Prior to Mass Spectrometric Analysis Gel-separated proteins were reduced, alkylated and digested in gel essentially following the procedure described by Shevchenko et al., 1996, Anal. Chem. 68:850-858. Briefly, gel-separated proteins were excised from the gel using a clean scalpel, reduced using 10 mM DTT (in 5 mM ammonium bicarbonate, 54° C., 45 min) and subsequently alkylated with 55 mM iodoacetamid (in 5 mM ammonium bicarbonate) at room temperature in the dark (30 minutes). Reduced and alkylated proteins were digested in gel with porcine trypsin (Promega) at a protease concentration of 12.5 ng/µl in 5 mM ammonium bicarbonate. Digestion was allowed to proceed for 4 hours at 37° C. and the reaction was subsequently stopped using 5 µl 5% formic acid.

4.2 Sample Preparation Prior to Analysis by Mass Spectrometry

Gel plugs were extracted twice with 20 µl 1% TFA and pooled with acidified digest supernatants. Samples were dried in a vacuum centrifuge and resuspended in 13 µl 1% TFA.

4.3. Mass Spectrometric Data Acquisition

Peptide samples were injected into a nano LC system (CapLC, Waters or Ultimate, Dionex) which was directly coupled either to a quadrupole TOF (QTOF2, QTOF Ultima, QTOF Micro, Micromass) or ion trap (LCQ Deca XP) mass spectrometer. Peptides were separated on the LC system using a gradient of aqueous and organic solvents (see below). Solvent A was 5% acetonitrile in 0.5% formic acid and solvent B was 70% acetonitrile in 0.5% formic acid.

TABLE 3

Peptides eluting off the LC system were partially sequenced within the mass spectrometer.

| Time (min) | % solvent A | % solvent B |
|---|---|---|
| 0 | 95 | 5 |
| 5.33 | 92 | 8 |
| 35 | 50 | 50 |
| 36 | 20 | 80 |
| 40 | 20 | 80 |
| 41 | 95 | 5 |
| 50 | 95 | 5 |

4.4. Protein Identification

The peptide mass and fragmentation data generated in the LC-MS/MS experiments were used to query fasta formatted protein and nucleotide sequence databases maintained and updated regularly at the NCBI (for the NCBInr, dbEST and the human and mouse genomes) and European Bioinformatics Institute (EBI, for the human, mouse, *D. melanogaster* and *C. elegans* proteome databases). Proteins were identified by correlating the measured peptide mass and fragmentation data with the same data computed from the entries in the database using the software tool Mascot (Matrix Science; Perkins et al., 1999. Probability-based protein identification by searching sequence databases using mass spectrometry data. Electrophoresis 20, 3551-3567). Search criteria varied depending on which mass spectrometer was used for the analysis.

TABLE 4

Peptide identification by mass spectrometry of LRRK2 from mouse brain (Experiment P11927B)

| Peptide number | Peptide position | Peptide sequence |
|---|---|---|
| 1 | 172-180 | YSANDEVQK |
| 2 | 454-466 | HAHAPEVAESGCK |
| 3 | 553-561 | FIGNPGIQK |
| 4 | 630-637 | ILASTLQR |
| 5 | 740-751 | GATSLIYQVCEK |
| 6 | 782-792 | GDSQVISLLLR |
| 7 | 832-841 | QTNTGSVLAR |
| 8 | 1016-1035 | LELHQNSLTSFPQQLCETLK |
| 9 | 1712-1723 | LLEISPFMLSGR |
| 10 | 1765-1771 | ITVPSC |
| 11 | 2031-2039 | TSEGTPGFR |
| 12 | 2406-2413 | HQLSYSGR |

EXAMPLE 3

Screening Assay for the Identification of LRRK2 Interacting Compounds

This examples describes a competitive binding assay in which test compounds are added directly into a cell lysate. Test compounds and the affinity matrix with the immobilized indol ligand 91 are added to lysate aliquots and allowed to bind to the proteins contained in the lysate sample. After the inbutation time the beads with captured proteins are separated from the lysate. Bound proteins are then eluted and the presence of LRRK2 in the eluate is detected and quantified using a specific antibody in a dot blot procedure and the Odyssey infrared detection system. By using various concentrations of a test compound a dose response curve is generated. Further experimental information is disclosed in WO2006/134056.

Washing of the Affinity Matrix

The affinity matrix as described in example 1 is washed two times with 1×DP buffer containing 0.4% NP40 and then resuspended in 1×DP buffer containing 0.4% NP40 (20% beads slurry).

TABLE 5

Preparation of 5× DP buffer

| Substance: | Stock solution | Final conc. in 1× lysis buffer | Add for 1 l 5× lysis buffer |
|---|---|---|---|
| Tris/HCl pH 7.5 | 1 M | 50 mM | 250 ml |
| Glycerol | 87% | 5% | 288 ml |
| MgCl$_2$ | 1 M | 1.5 mM | 7.5 ml |
| NaCl | 5 M | 150 mM | 150 ml |
| Na$_3$VO$_4$ | 100 mM | 1 mM | 50 ml |

The five-fold concentrated (5×) DP buffer is filtered through a 0.22 μm filter and stored at −80° C. In order to obtain 1×DP buffer the 5×DP buffer is diluted 1:5 with distilled water. Stock solutions are obtained from the following suppliers: 1.0 M Tris/HCl pH 7.5 (Sigma, T-2663), 87% Glycerol (Merck, catalogue number 04091.2500); 1.0 M MgCl$_2$ (Sigma, M-1028); 5.0 M NaCl (Sigma, S-5150).

Preparation of Test Compounds

Stock solutions of test compounds are prepared in DMSO corresponding to a 100 fold higher concentration compared to the final desired test concentration (e.g. a 400 μM stock solution is prepared for a final test concentration of 4 μM). This dilution scheme results in a final DMSO concentration of 1% in the assay. For control experiments (no test compound) a buffer containing 1% DMSO is used so that all samples contain 1% DMSO.

Preparation and Dilution of Cell Lysate

The cell lysate is prepared as described in example 2. For a typical experiment one lysate aliquot containing 50 mg of protein is thawed in a 37° C. water bath and then kept at 4° C. To the lysate one volume of 1×DP buffer is added so that a final NP40 concentration of 0.4% is achieved. Then, 1/50 of the final volume of a 50 fold concentrated protease inhibitor solution is added (1 tablet of protease inhibitor dissolved in 0.5 ml of 1×DP buffer containing 0.4% NP40; EDTA-free tablet protease inhibitor cocktail from Roche Diagnostics, catalogue number 41647). The lysate is further diluted by adding 1×DP buffer containing 0.4% NP40 so that a final protein concentration of 5 mg/ml is achieved.

Incubation of Lysate with Test Compound and Affinity Matrix

A volume of 100 μl of diluted lysate is dispensed into each well of a 96 well filter plate. Then 1.5 μl of test compound diluted in DMSO is added. For control reactions 1.5 μl DMSO without test compound is used. Then 50 μl of affinity matrix (20% slurry) per well are added. The plate is incubated for two hours at 4° C. on a shaker. The plate is washed using a vacuum manifold instrument (Millipore, MAVM 096 0R). Each well is washed four times with 400 μl of 1×DP buffer containing 0.4% NP-40 and two times with 400 μl 1×DP buffer containing 0.2% NP-40.

For elution the filter plate is placed on a collection plate and 40 μl of 2× sample buffer (100 mM TrisHCl, pH6.8; 4% SDS; 20% glycerol; 0.02% Bromphenol blue) with DTT (50 mM final concentration) is added to each well. The plates are incubated for 30 minutes at room temperature on a shaker (750 rpm on a Thermomixer, Eppendorf). Subsequently the plates are centrifuged for 2 minutes at 1100 rpm (Heraeus centrifuge) and the eluate is collected in the wells of the collection plate.

Detection and Quantification of Eluted LRRK2

The LRRK2 protein in the eluates is detected and quantified by a dot blot procedure using a first antibody directed against LRRK2 (Santa Cruz Biotechnology, Santa Cruz, Calif., USA) and a fluorescently labeled secondary antibody (anti-mouse IRDye™ 800, from Rockland, 610-732-124). The Odyssey Infrared Imaging system from LI-COR Biosciences (Lincoln, Nebr., USA) is operated according to instructions provided by the manufacturer (Schutz-Geschwendener et al., 2004. Quantitative, two-color Western blot detection with infrared fluorescence. Published May 2004 by LI-COR Biosciences, www.licor.com).

The dot blot apparatus is used according to the instructions of the supplier (Bio-Dot microfiltration apparatus, BioRad 170-65). Nitrocellulose membranes (BioTrace NT Nitrocellulose, PALL BTNT30R) are treated with 20% ethanol and subsequently washed with 1×PBS buffer. Per dot 30 μl of eluate sample are applied.

For the detection of LRRK2 the membranes are first blocked by incubation with Odyssey blocking buffer (LI-COR, 927-40000) for one hour at room temperature. Blocked membranes are then incubated for 16 hours at 4° C. with the anti-LRRK2 antibody which is diluted in Odyssey blocking buffer containing 0.2% Tween-20. After washing the membrane four times with 1×PBS buffer containing 0.1% Tween 20 the membrane is incubated for 40 minutes with the detection antibody (anti-mouse IRDye™ 800 from Rockland, 610-732-124) diluted in Odyssey blocking buffer containing 0.2% Tween-20. Afterwards the membrane is washed four times for five minutes each with 1×PBS buffer/0.1% Tween 20 and once for 5 minutes with 1×PBS buffer. The membrane is kept in PBS buffer at 4° C. and then scanned with the Odyssey instrument and signals are recorded and analysed according to the instructions of the manufacturer.

EXAMPLE 4

LRRK2 Kinase Assay

This example describes an assay that can be used to determine whether a LRRK2 interacting compound is a LRRK2 kinase inhibitor. The assay is performed as described previously (West et al., 2005. PNAS 102, 16842-16847).

A full-length LRRK2 cDNA clone with a Myc epitope tag is cloned into a mammalian expression vector. The expression plasmid is transiently transfected into HEK-293T cells by using the FuGENE 6.0 reagent (Roche Applied Science) according to the manufacturer's instructions. HEK-293T cells are cultured in Opti-MEM media (Invitrogen) supplemented with 10% FBS, penicillin (100 units/ml), and streptomycin (100 µg/ml). To prepare recombinant LRRK2 protein for kinase assays HEK-293T cells are harvested in immunoprecipitation buffer (0.5% Triton-X-100, 1× complete mini protease inhibitor cocktail (Roche) in PBS) and the lysates are incubated at 4° C. for one hour followed by centrifugation at 17,500×g for 15 minutes. The supernatant fraction is combined with Protein G sepharose 4 Fast Flow (Amersham Pharmacia Biotech) precomplexed with the mouse monoclonal anti-c-myc antibody (clone 9E10; Roche) followed by incubation overnight with rotating the tube. The protein G Sepharose complex is pelleted by centrifugation and washed five times with buffer supplemented with 500 mM NaCl and once with 1×PBS buffer.

Myc-tagged LRRK2 protein bound to G sepharose is resuspended in kinase buffer (20 mM Hepes, pH7.4; 15 mM $MgCl_2$; 5 mM EGTA; 20 mM beta-glycerol phosphate) on ice together with 25 µM biotinylated myelin basic protein (MBP; Upstate Biotechnology, Lake Placid, N.Y.). The kinase reaction is initiated by adding 0.5 µCi of [gamma$^{32}$P]ATP (Perkin Elmer) and 15 µM ATP. The mixture is incubated at 30° C. for 15 minutes. The reaction is placed on ice and terminated by adding 2.5 M guanidine-HCl. The universal kinase assay kit (Calbiochem) is used to quantify incorporated radioisotope in biotinylated MBP by adding avidin solution (Calbiochem) to the reaction and incubating at 25° C. for 10 minutes. The reaction is centrifuged at 800×g for two minutes and the supernatant is placed on a column containing an avidin binding membrane and washed according to the manufacturer's protocol. The amount of incorporated radioisotope is measured by liquid scintillation counting.

The LRRK2 autophosphorylation activity is determined in a kinase reaction as described above except that no MBP is added. The reaction is incubated for 15 minutes at 30° C. and terminated by adding Laemmli sample buffer containing 5% 2-mercaptoethanol. The reactions are heated for 10 minutes at 75° C. and then placed on ice. After brief centrifugation the samples (supernatants) are separated in a 6% SDS-Polyacrylamide gel, transferred to a poly-vinylidinedifluoride (PVDF) membrane and exposed to BioMax film (Kodak). The membrane is probed with an anti-c-myc antibody (9E10; Roche) to determine the amount of LRRK2 in each reaction. The autoradiography and Western blot bands are quantified by using IMAGEQUANT 5.0 thereby normalizing the amount of phosphorylated MBP to the amount of LRRK2 in each experiment.

The invention claimed is:

1. A method for the identification of a compound that is an inhibitor of the kinase activity of mutant leucine-rich repeat kinase 2 (LRRK2), comprising the steps of
   a) providing a protein preparation containing wild type or mutant LRRK2,
   b) contacting the protein preparation with indol ligand 91 immobilized on a solid support under conditions allowing the formation of a complex of indol ligand 91 with LRRK2 of a),
   c) incubating the indol ligand 91-LRRK2 complex with a given compound, and
   d) determining whether the compound separates LRRK2 of a) from the immobilized indol ligand 91;
   wherein step d) comprises the detection of separated or bound LRRK2 of a) or the determination of the amount of separated or bound LRRK2 of a); wherein separation of LRRK2 of a) from indol ligand 91 by said compound indicates that said compound interacts with LRRK2 of a); and
   e) determining whether said compound that interacts with LRRK2 of a) is an inhibitor of the kinase activity of mutant LRRK2, wherein said mutant LRRK2 has the same or different amino acid sequence as the LRRK2 of a),
   wherein each mutant LRRK2 of a) and e) is independently selected from the group consisting of: G2019S, R1441C, Y1699C, I2020T, R793M, Q930R, R1067Q, S1096C, I1122V, S1228T, I1371V, R1441G, R1441H, R1514Q, M1869T, R1941H, I2012T, T2356I, and G2385R.

2. The method of claim 1, wherein LRRK2 is detected or the amount of LRRK2 is determined in step d) by mass spectrometry or immunodetection methods.

3. The method of claim 1, performed as a medium or high throughput screening.

4. The method of claim 1, wherein said compound is selected from the group consisting of synthetic compounds, organic synthetic drugs, small molecule organic drugs, and natural small molecule compounds.

5. The method of claim 1, wherein the solid support is selected from the group consisting of agarose, modified agarose, sepharose beads, latex, cellulose, and ferro- or ferrimagnetic particles.

6. The method of claim 1, wherein indol ligand 91 is covalently coupled to the solid support.

7. The method of claim 1, wherein said mutant LRRK2 is associated with the occurrence of Parkinson's disease.

8. The method of claim 1, wherein said LRRK2 of a) is wildtype.

9. A method for the identification of a compound that is an inhibitor of the kinase activity of mutant LRRK2, comprising the steps of
   a) providing a first protein preparation containing wild type or mutant LRRK2,
   b) contacting the first protein preparation with indol ligand 91 immobilized on a solid support and with a first given compound under conditions allowing the formation of a complex of indol ligand 91 with LRRK2 of a), and
   c) detecting the indol ligand 91-LRRK2 complex formed in step b);
   d) providing a second protein preparation containing wild type or mutant LRRK2;
   e) contacting the second protein preparation with indol ligand 91 immobilized on a solid support and with a second given compound under conditions allowing the formation of a complex of indol ligand 91 with LRRK2 of d);
   f) detecting the indol ligand 91-LRRK2 complex formed in step e);
   wherein a reduced amount of indol ligand-LRRK2 complex formed in step b) in comparison to step e) indicates that the first compound has a stronger interaction with LRRK2 than the second compound; and
   g) determining whether the first compound is an inhibitor of the kinase activity of mutant LRRK2, wherein said mutant LRRK2 has the same or different amino acid sequence as the LRRK2 of a) or d),
   wherein each mutant LRRK2 of a), d), and g) is independently selected from the group consisting of: G2019S, R1441C, Y1699C, I2020T, R793M, Q930R, R1067Q, S1096C, I1122V, S1228T, I1371V, R1441G, R1441H, R1514Q, M1869T, R1941H, I2012T, T2356I, and G2385R.

10. The method of claim 9, wherein the amount of indol ligand 91-LRRK2 complex is determined in c) or f) by separating LRRK2 of a) or d) from the immobilized indol ligand 91 and subsequently determining the amount of LRRK2 of a) or d).

11. The method of claim 10, wherein the amount of LRRK2 is determined in steps c) or f) by mass spectrometry or immunodetection methods.

12. The method of claim 9, performed as a medium or high throughput screening.

13. The method of claim 9, wherein said compound is selected from the group consisting of synthetic compounds, organic synthetic drugs, small molecule organic drugs, and natural small molecule compounds.

14. The method of claim 9, wherein the solid support is selected from the group consisting of agarose, modified agarose, sepharose beads, latex, cellulose, and ferro- or ferrimagnetic particles.

15. The method of claim 9, wherein indol ligand 91 is covalently coupled to the solid support in a) or e).

16. The method of claim 9, wherein said mutant LRRK2 is associated with the occurrence of Parkinson's disease.

17. The method of claim 9, wherein said LRRK2 of a) or d) is wildtype.

18. A method for the identification of a compound that is an inhibitor of the activity of mutant LRRK2, comprising the steps of:
   a) providing two aliquots of a protein preparation containing wild type or mutant LRRK2,
   b) contacting one aliquot with indol ligand 91 immobilized on a solid support under conditions allowing the formation of a complex of indol ligand 91 with LRRK2 of a),
   c) contacting the other aliquot with indol ligand 91 immobilized on a solid support and with a given compound under conditions allowing the formation of a complex of indol ligand 91 with LRRK2 of a),
   d) determining the amount of indol ligand 91-LRRK2 complex formed in steps b) and c);
   wherein a reduced amount of indol ligand 91-LRRK2 formed in step c) in comparison to step b) indicates that the compound interacts with LRRK2 of a); and
   e) determining whether the compound that interacts with LRRK2 of a) is an inhibitor of the kinase activity of mutant LRRK2, wherein said mutant LRRK2 has the same or different amino acid sequence as the LRRK2 of a),
   wherein each mutant LRRK2 of a) and e) is independently selected from the group consisting of: G2019S, R1441C, Y1699C, I2020T, R793M, Q930R, R1067Q, S1096C, I1122V, S1228T, I1371V, R1441G, R1441H, R1514Q, M1869T, R1941H, I2012T, T2356I, and G2385R.

19. The method of claim 18, wherein the amount of indol ligand 91-LRRK2 complex is determined in step d) by separating LRRK2 of a) from the immobilized indol ligand 91 and subsequently determining the amount of LRRK2 of a).

20. The method of claim 19, wherein the amount of LRRK2 of a) is determined by mass spectrometry or immunodetection methods.

21. The method of claim 18, performed as a medium or high throughput screening.

22. The method of claim 18, wherein said compound is selected from the group consisting of synthetic compounds, organic synthetic drugs, small molecule organic drugs, and natural small molecule compounds.

23. The method of claim 18, wherein the solid support is selected from the group consisting of agarose, modified agarose, sepharose beads, latex, cellulose, and ferro- or ferrimagnetic particles.

24. The method of claim 18, wherein indol ligand 91 is covalently coupled to the solid support.

25. The method of claim 18, wherein said mutant LRRK2 is associated with the occurrence of Parkinson's disease.

26. The method of claim 18, wherein said LRRK2 of a) is wildtype.

* * * * *

SEQUENCE LISTING

<160> NUMBER OF SEQ ID NOS: 13

<210> SEQ ID NO 1
<211> LENGTH: 2527
<212> TYPE: PRT
<213> ORGANISM: Mus Musculus

<400> SEQUENCE: 1

Met Ala Ser Gly Ala Cys Gln Gly Cys Glu Glu Glu Glu Glu Glu
1               5                   10                  15

Ala Leu Lys Lys Leu Ile Val Arg Leu Asn Asn Val Gln Glu Gly Lys
                20                  25                  30

Gln Ile Glu Thr Leu Leu Gln Leu Leu Glu Asp Met Leu Val Phe Thr
            35                  40                  45

Tyr Ser Asp Arg Ala Ser Lys Leu Phe Glu Asp Lys Asn Phe His Val
        50                  55                  60

Pro Leu Leu Ile Val Leu Asp Ser Tyr Met Arg Val Ala Ser Val Gln
65                  70                  75                  80

Gln Ala Gly Trp Ser Leu Leu Cys Lys Leu Ile Glu Val Cys Pro Gly
                85                  90                  95

Thr Leu Gln Ser Leu Ile Gly Pro Gln Asp Ile Gly Asn Asp Trp Glu
            100                 105                 110

```
Val Leu Gly Ile His Arg Leu Ile Leu Lys Met Leu Thr Val His His
            115                 120                 125

Ala Asn Val Asn Leu Ser Ile Val Gly Leu Lys Ala Leu Asp Leu Leu
            130                 135                 140

Leu Asp Ser Gly Lys Leu Thr Leu Leu Ile Leu Asp Glu Glu Cys Asp
145                 150                 155                 160

Ile Phe Leu Leu Ile Phe Asp Ala Met His Arg Tyr Ser Ala Asn Asp
                165                 170                 175

Glu Val Gln Lys Leu Gly Cys Lys Ala Leu His Val Leu Phe Glu Arg
                180                 185                 190

Val Ser Glu Glu Gln Leu Thr Glu Phe Val Glu Asn Lys Asp Tyr Thr
            195                 200                 205

Ile Leu Leu Ser Thr Phe Gly Ser Phe Arg Arg Asp Lys Glu Ile Val
            210                 215                 220

Tyr His Val Leu Cys Cys Leu His Ser Leu Ala Val Thr Cys Ser Asn
225                 230                 235                 240

Val Glu Val Leu Met Ser Gly Asn Val Arg Cys Tyr Asn Leu Val Val
                245                 250                 255

Glu Ala Met Lys Ala Phe Pro Thr Asn Glu Asn Ile Gln Glu Val Ser
            260                 265                 270

Cys Ser Leu Phe Gln Lys Leu Thr Leu Gly Asn Phe Phe Asn Ile Leu
            275                 280                 285

Val Leu Asn Glu Val His Val Phe Val Val Lys Ala Val Arg Gln Tyr
290                 295                 300

Pro Glu Asn Ala Ala Leu Gln Ile Ser Ala Leu Ser Cys Leu Ala Leu
305                 310                 315                 320

Leu Thr Glu Thr Ile Phe Leu Asn Gln Asp Leu Glu Glu Arg Ser Glu
                325                 330                 335

Thr Gln Glu Gln Ser Glu Glu Asp Ser Glu Lys Leu Phe Trp Leu
            340                 345                 350

Glu Pro Cys Tyr Lys Ala Leu Val Arg His Arg Lys Asp Lys His Val
            355                 360                 365

Gln Glu Ala Ala Cys Trp Ala Leu Asn Asn Leu Leu Met Tyr Gln Asn
            370                 375                 380

Ser Leu His Glu Lys Ile Gly Asp Glu Asp Gly Gln Phe Pro Ala His
385                 390                 395                 400

Arg Glu Val Met Leu Ser Met Leu Met His Ser Ser Lys Asp Val
                405                 410                 415

Phe Gln Ala Ala Ala His Ala Leu Ser Thr Leu Leu Glu Gln Asn Val
            420                 425                 430

Asn Phe Arg Lys Ile Leu Leu Ala Lys Gly Val Tyr Leu Asn Val Leu
            435                 440                 445

Glu Leu Met Gln Lys His Ala His Ala Pro Glu Val Ala Glu Ser Gly
450                 455                 460

Cys Lys Met Leu Ser His Leu Phe Glu Gly Ser Asn Pro Ser Leu Asp
465                 470                 475                 480

Thr Met Ala Ala Val Pro Lys Ile Leu Thr Val Met Lys Ala His
                485                 490                 495

Gly Thr Ser Leu Ser Val Gln Leu Glu Ala Leu Arg Ala Ile Leu His
            500                 505                 510

Phe Val Val Pro Gly Leu Leu Glu Glu Ser Arg Glu Asp Ser Gln Cys
            515                 520                 525

Arg Pro Asn Val Leu Arg Lys Gln Cys Phe Arg Thr Asp Ile His Lys
530                 535                 540
```

```
Leu Val Leu Val Ala Leu Asn Arg Phe Ile Gly Asn Pro Gly Ile Gln
545                 550                 555                 560

Lys Cys Gly Leu Lys Val Ile Ser Ser Leu Ala His Leu Pro Asp Ala
                565                 570                 575

Thr Glu Thr Leu Ser Leu Gln Gly Ala Val Asp Ser Val Leu His Thr
                580                 585                 590

Leu Gln Met Tyr Pro Asp Asp Gln Glu Ile Gln Cys Leu Gly Leu His
            595                 600                 605

Leu Met Gly Cys Leu Met Thr Lys Lys Asn Phe Cys Ile Gly Thr Gly
        610                 615                 620

His Leu Leu Ala Lys Ile Leu Ala Ser Thr Leu Gln Arg Phe Lys Asp
625                 630                 635                 640

Val Ala Glu Val Gln Thr Thr Gly Leu Gln Thr Thr Leu Ser Ile Leu
                645                 650                 655

Glu Leu Ser Val Ser Phe Ser Lys Leu Leu Val His Tyr Ser Phe Asp
                660                 665                 670

Val Val Ile Phe His Gln Met Ser Ser Ser Val Val Glu Gln Lys Asp
            675                 680                 685

Glu Gln Phe Leu Asn Leu Cys Cys Lys Cys Phe Ala Lys Val Ala Val
    690                 695                 700

Asp Asp Glu Leu Lys Asn Thr Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Val Lys Gly Ala Thr Ser Leu Ile Tyr Gln Val Cys Glu Lys Glu
                740                 745                 750

Ser Ser Pro Lys Leu Val Glu Leu Leu Leu Asn Gly Gly Cys Arg Glu
            755                 760                 765

Gln Asp Val Arg Lys Ala Leu Thr Ile Ser Ile Gln Lys Gly Asp Ser
    770                 775                 780

Gln Val Ile Ser Leu Leu Leu Arg Lys Leu Ala Leu Asp Leu Ala Asn
785                 790                 795                 800

Asn Ser Ile Cys Leu Gly Gly Phe Gly Ile Gly Lys Ile Asp Pro Ser
                805                 810                 815

Trp Leu Gly Pro Leu Phe Pro Asp Lys Ser Ser Asn Leu Arg Lys Gln
            820                 825                 830

Thr Asn Thr Gly Ser Val Leu Ala Arg Lys Val Leu Arg Tyr Gln Met
        835                 840                 845

Arg Asn Thr Leu Gln Glu Gly Val Ala Ser Gly Ser Asp Gly Asn Phe
850                 855                 860

Ser Glu Asp Ala Leu Ala Lys Phe Gly Glu Trp Thr Phe Ile Pro Asp
865                 870                 875                 880

Ser Ser Met Asp Ser Val Phe Gly Gln Ser Asp Asp Leu Asp Ser Glu
                885                 890                 895

Gly Ser Glu Ser Ser Phe Leu Val Lys Arg Lys Ser Asn Ser Ile Ser
            900                 905                 910

Val Gly Glu Val Tyr Arg Asp Leu Ala Leu Gln Arg Tyr Ser Pro Asn
        915                 920                 925

Ala Gln Arg His Ser Asn Ser Leu Gly Pro Val Phe Asp His Glu Asp
    930                 935                 940

Leu Leu Arg Arg Lys Arg Lys Ile Leu Ser Ser Asp Glu Ser Leu Arg
945                 950                 955                 960

Ser Ser Arg Leu Pro Ser His Met Arg Gln Ser Asp Ser Ser Ser Ser
```

-continued

```
                965                 970                 975
Leu Ala Ser Glu Arg Glu His Ile Thr Ser Leu Asp Leu Ser Ala Asn
            980                 985                 990
Glu Leu Lys Asp Ile Asp Ala Leu  Ser Gln Lys Cys Cys  Leu Ser Ser
            995                 1000                1005
His Leu Gly His Leu Thr Lys Leu Glu Leu His Gln  Asn Ser Leu
    1010                1015                1020
Thr Ser  Phe Pro Gln Gln Leu  Cys Glu Thr Leu Lys  Cys Leu Ile
    1025                1030                1035
His Leu  Asp Leu His Ser Asn  Lys Phe Thr Ser Phe  Pro Ser Phe
    1040                1045                1050
Val Leu  Lys Met Pro Arg Ile  Thr Asn Leu Asp Ala  Ser Arg Asn
    1055                1060                1065
Asp Ile  Gly Pro Thr Val Val  Leu Asp Pro Ala Met  Lys Cys Pro
    1070                1075                1080
Ser Leu  Lys Gln Leu Asn Leu  Ser Tyr Asn Gln Leu  Ser Ser Ile
    1085                1090                1095
Pro Glu  Asn Leu Ala Gln Val  Val Glu Lys Leu Glu  Gln Leu Leu
    1100                1105                1110
Leu Glu  Gly Asn Lys Ile Ser  Gly Ile Cys Ser Pro  Leu Ser Leu
    1115                1120                1125
Lys Glu  Leu Lys Ile Leu Asn  Leu Ser Lys Asn His  Ile Pro Ser
    1130                1135                1140
Leu Pro  Gly Asp Phe Leu Glu  Ala Cys Ser Lys Val  Glu Ser Phe
    1145                1150                1155
Ser Ala  Arg Met Asn Phe Leu  Ala Ala Met Pro Ala  Leu Pro Ser
    1160                1165                1170
Ser Ile  Thr Ser Leu Lys Leu  Ser Gln Asn Ser Phe  Thr Cys Ile
    1175                1180                1185
Pro Gly  Ala Ile Phe Ser Leu  Pro His Leu Arg Ser  Leu Asp Met
    1190                1195                1200
Ser His  Asn Asn Ile Glu Cys  Leu Pro Gly Pro Ala  His Trp Lys
    1205                1210                1215
Ser Leu  Asn Leu Arg Glu Leu  Ile Phe Ser Lys Asn  Gln Ile Ser
    1220                1225                1230
Thr Leu  Asp Phe Ser Glu Asn  Pro His Val Trp Ser  Arg Val Glu
    1235                1240                1245
Lys Leu  His Leu Ser His Asn  Lys Leu Lys Glu Ile  Pro Pro Glu
    1250                1255                1260
Ile Gly  Cys Leu Glu Asn Leu  Thr Ser Leu Asp Val  Ser Tyr Asn
    1265                1270                1275
Leu Glu  Leu Arg Ser Phe Pro  Asn Glu Met Gly Lys  Leu Ser Lys
    1280                1285                1290
Ile Trp  Asp Leu Pro Leu Asp  Gly Leu His Leu Asn  Phe Asp Phe
    1295                1300                1305
Lys His  Val Gly Cys Lys Ala  Lys Asp Ile Ile Arg  Phe Leu Gln
    1310                1315                1320
Gln Arg  Leu Lys Lys Ala Val  Pro Tyr Asn Arg Met  Lys Leu Met
    1325                1330                1335
Ile Val  Gly Asn Thr Gly Ser  Gly Lys Thr Thr Leu  Leu Gln Gln
    1340                1345                1350
Leu Met  Lys Met Lys Lys Pro  Glu Leu Gly Met Gln  Gly Ala Thr
    1355                1360                1365
```

-continued

| | | | | | | | | | | |
|---|---|---|---|---|---|---|---|---|---|---|
| Val | Gly 1370 | Ile | Asp | Val 1375 | Arg | Asp | Trp | Ser | Ile 1380 | Gln | Ile | Arg | Gly | Lys |
| Arg | Arg 1385 | Lys | Asp | Leu | Val 1390 | Leu | Asn | Val | Trp | Asp 1395 | Phe | Ala | Gly | Arg |
| Glu | Glu 1400 | Phe | Tyr | Ser | Thr 1405 | His | Pro | His | Phe | Met 1410 | Thr | Gln | Arg | Ala |
| Leu | Tyr 1415 | Leu | Ala | Val | Tyr 1420 | Asp | Leu | Ser | Lys | Gly 1425 | Gln | Ala | Glu | Val |
| Asp | Ala 1430 | Met | Lys | Pro | Trp 1435 | Leu | Phe | Asn | Ile | Lys 1440 | Ala | Arg | Ala | Ser |
| Ser | Ser 1445 | Pro | Val | Ile | Leu 1450 | Val | Gly | Thr | His | Leu 1455 | Asp | Val | Ser | Asp |
| Glu | Lys 1460 | Gln | Arg | Lys | Ala 1465 | Cys | Ile | Ser | Lys | Ile 1470 | Thr | Lys | Glu | Leu |
| Leu | Asn 1475 | Lys | Arg | Gly | Phe 1480 | Pro | Thr | Ile | Arg | Asp 1485 | Tyr | His | Phe | Val |
| Asn | Ala 1490 | Thr | Glu | Glu | Ser 1495 | Asp | Ala | Leu | Ala | Lys 1500 | Leu | Arg | Lys | Thr |
| Ile | Ile 1505 | Asn | Glu | Ser | Leu 1510 | Asn | Phe | Lys | Ile | Arg 1515 | Asp | Gln | Pro | Val |
| Val | Gly 1520 | Gln | Leu | Ile | Pro 1525 | Asp | Cys | Tyr | Val | Glu 1530 | Leu | Glu | Lys | Ile |
| Ile | Leu 1535 | Ser | Glu | Arg | Lys 1540 | Ala | Val | Pro | Thr | Glu 1545 | Phe | Pro | Val | Ile |
| Asn | Arg 1550 | Lys | His | Leu | Leu 1555 | Gln | Leu | Val | Asn | Glu 1560 | His | Gln | Leu | Gln |
| Leu | Asp 1565 | Glu | Asn | Glu | Leu 1570 | Pro | His | Ala | Val | His 1575 | Phe | Leu | Asn | Glu |
| Ser | Gly 1580 | Val | Leu | Leu | His 1585 | Phe | Gln | Asp | Pro | Ala 1590 | Leu | Gln | Leu | Ser |
| Asp | Leu 1595 | Tyr | Phe | Val | Glu 1600 | Pro | Lys | Trp | Leu | Cys 1605 | Lys | Val | Met | Ala |
| Gln | Ile 1610 | Leu | Thr | Val | Lys 1615 | Val | Asp | Gly | Cys | Leu 1620 | Lys | His | Pro | Lys |
| Gly | Ile 1625 | Ile | Ser | Arg | Arg 1630 | Asp | Val | Glu | Lys | Phe 1635 | Leu | Ser | Lys | Lys |
| Lys | Arg 1640 | Phe | Pro | Lys | Asn 1645 | Tyr | Met | Met | Gln | Tyr 1650 | Phe | Lys | Leu | Leu |
| Glu | Lys 1655 | Phe | Gln | Ile | Ala 1660 | Leu | Pro | Ile | Gly | Glu 1665 | Glu | Tyr | Leu | Leu |
| Val | Pro 1670 | Ser | Ser | Leu | Ser 1675 | Asp | His | Arg | Pro | Val 1680 | Ile | Glu | Leu | Pro |
| His | Cys 1685 | Glu | Asn | Ser | Glu 1690 | Ile | Ile | Arg | Leu | Tyr 1695 | Glu | Met | Pro | |
| Tyr | Phe 1700 | Pro | Met | Gly | Phe 1705 | Trp | Ser | Arg | Leu | Ile 1710 | Asn | Arg | Leu | Leu |
| Glu | Ile 1715 | Ser | Pro | Phe | Met 1720 | Leu | Ser | Gly | Arg | Glu 1725 | Arg | Ala | Leu | Arg |
| Pro | Asn 1730 | Arg | Met | Tyr | Trp 1735 | Arg | Gln | Gly | Ile | Tyr 1740 | Leu | Asn | Trp | Ser |
| Pro | Glu 1745 | Ala | Tyr | Cys | Leu 1750 | Val | Gly | Ser | Glu | Val 1755 | Leu | Asp | Asn | Arg |
| Pro | Glu 1760 | Ser | Phe | Leu | Lys 1765 | Ile | Thr | Val | Pro | Ser 1770 | Cys | Arg | Lys | Gly |

-continued

```
Cys Ile Leu Leu Gly Arg Val Val Asp His Ile Asp Ser Leu Met
    1775            1780            1785

Glu Glu Trp Phe Pro Gly Leu Leu Glu Ile Asp Ile Cys Gly Glu
    1790            1795            1800

Gly Glu Thr Leu Leu Lys Lys Trp Ala Leu Tyr Ser Phe Asn Asp
    1805            1810            1815

Gly Glu Glu His Gln Lys Ile Leu Leu Asp Glu Leu Met Lys Lys
    1820            1825            1830

Ala Glu Glu Gly Asp Leu Leu Ile Asn Pro Asp Gln Pro Arg Leu
    1835            1840            1845

Thr Ile Pro Ile Ser Gln Ile Ala Pro Asp Leu Ile Leu Ala Asp
    1850            1855            1860

Leu Pro Arg Asn Ile Met Leu Asn Asn Asp Glu Leu Glu Phe Glu
    1865            1870            1875

Glu Ala Pro Gly Phe Leu Leu Gly Asp Gly Ser Phe Gly Ser Val
    1880            1885            1890

Tyr Arg Ala Ala Tyr Glu Gly Glu Glu Val Ala Val Lys Ile Phe
    1895            1900            1905

Asn Lys His Thr Ser Leu Arg Leu Leu Arg Gln Glu Leu Val Val
    1910            1915            1920

Leu Cys His Leu His His Pro Ser Leu Ile Ser Leu Leu Ala Ala
    1925            1930            1935

Gly Ile Arg Pro Arg Met Leu Val Met Glu Leu Ala Ser Lys Gly
    1940            1945            1950

Ser Leu Asp Arg Leu Leu Gln Gln Asp Lys Ala Ser Leu Thr Arg
    1955            1960            1965

Thr Leu Gln His Arg Ile Ala Leu His Val Ala Asp Gly Leu Arg
    1970            1975            1980

Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu His Asp Ile Trp Thr Thr Gly Ser Arg Ile
    2060            2065            2070

Met Glu Gly Leu Arg Phe Pro Asn Glu Phe Asp Glu Leu Ala Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Thr Lys Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Ile Cys Leu Met Arg His Ile Leu Ile Pro Lys
    2135            2140            2145

Asn Ile Ile Val Glu Cys Met Val Ala Thr Asn Leu Asn Ser Lys
    2150            2155            2160

Ser Ala Thr Leu Trp Leu Gly Cys Gly Asn Thr Glu Lys Gly Asn
```

-continued

```
                2165                2170                2175

Leu Ser Leu Phe Asp Leu Asn Thr Glu Arg Tyr Ser Tyr Glu Glu
        2180                2185                2190

Val Ala Asp Ser Arg Ile Leu Cys Leu Ala Leu Val His Leu Ala
        2195                2200                2205

Ala Glu Lys Glu Ser Trp Val Val Cys Gly Thr Gln Ser Gly Ala
        2210                2215                2220

Leu Leu Val Ile Asn Val Glu Glu Thr Lys Arg His Thr Leu
        2225                2230                2235

Glu Lys Met Thr Asp Ser Val Thr Cys Leu His Cys Asn Ser Leu
        2240                2245                2250

Ala Lys Gln Ser Lys Gln Ser Asn Phe Leu Leu Val Gly Thr Ala
        2255                2260                2265

Asp Gly Asn Leu Met Ile Phe Glu Asp Lys Ala Val Lys Cys Lys
        2270                2275                2280

Gly Ala Ala Pro Leu Lys Thr Leu His Ile Gly Asp Val Ser Thr
        2285                2290                2295

Pro Leu Met Cys Leu Ser Glu Ser Leu Asn Ser Ser Glu Arg His
        2300                2305                2310

Ile Thr Trp Gly Gly Cys Gly Thr Lys Val Phe Ser Phe Ser Asn
        2315                2320                2325

Asp Phe Thr Ile Gln Lys Leu Ile Glu Thr Lys Thr Asn Gln Leu
        2330                2335                2340

Phe Ser Tyr Ala Ala Phe Ser Asp Ser Asn Ile Ile Ala Leu Ala
        2345                2350                2355

Val Asp Thr Ala Leu Tyr Ile Ala Lys Lys Asn Ser Pro Val Val
        2360                2365                2370

Glu Val Trp Asp Lys Lys Thr Glu Lys Leu Cys Glu Leu Ile Asp
        2375                2380                2385

Cys Val His Phe Leu Lys Glu Val Met Val Lys Leu Asn Lys Glu
        2390                2395                2400

Ser Lys His Gln Leu Ser Tyr Ser Gly Arg Val Lys Ala Leu Cys
        2405                2410                2415

Leu Gln Lys Asn Thr Ala Leu Trp Ile Gly Thr Gly Gly Gly His
        2420                2425                2430

Ile Leu Leu Leu Asp Leu Ser Thr Arg Arg Val Ile Arg Thr Ile
        2435                2440                2445

His Asn Phe Cys Asp Ser Val Arg Ala Met Ala Thr Ala Gln Leu
        2450                2455                2460

Gly Ser Leu Lys Asn Val Met Leu Val Leu Gly Tyr Lys Arg Lys
        2465                2470                2475

Ser Thr Glu Gly Ile Gln Glu Gln Lys Glu Ile Gln Ser Cys Leu
        2480                2485                2490

Ser Ile Trp Asp Leu Asn Leu Pro His Glu Val Gln Asn Leu Glu
        2495                2500                2505

Lys His Ile Glu Val Arg Thr Glu Leu Ala Asp Lys Met Arg Lys
        2510                2515                2520

Thr Ser Val Glu
        2525

<210> SEQ ID NO 2
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 2

Tyr Ser Ala Asn Asp Glu Val Gln Lys
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

His Ala His Ala Pro Glu Val Ala Glu Ser Gly Cys Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Phe Ile Gly Asn Pro Gly Ile Gln Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Ile Leu Ala Ser Thr Leu Gln Arg
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Gly Ala Thr Ser Leu Ile Tyr Gln Val Cys Glu Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Gly Asp Ser Gln Val Ile Ser Leu Leu Leu Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 8

Gln Thr Asp Thr Gly Ser Val Leu Ala Arg
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Leu Glu Leu His Gln Asp Ser Leu Thr Ser Phe Pro Gln Gln Leu Cys
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Leu Leu Glu Ile Ser Pro Phe Met Leu Ser Gly Arg
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Ile Thr Val Pro Ser Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Thr Ser Glu Gly Thr Pro Gly Phe Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

His Gln Leu Ser Tyr Ser Gly Arg
1               5
```